(12) United States Patent
Jury

(10) Patent No.: US 9,814,604 B2
(45) Date of Patent: Nov. 14, 2017

(54) GRIPPING DEVICE

(71) Applicant: 5TH ELEMENT LIMITED, Lower Hutt (NZ)

(72) Inventor: Mathew James Jury, Lower Hutt (NZ)

(73) Assignee: 5th Element Limited, Lower Hutt (NZ)

( * ) Notice: Subject to any disclaimer, the term of this patent is extended or adjusted under 35 U.S.C. 154(b) by 0 days.

(21) Appl. No.: 14/420,706

(22) PCT Filed: Aug. 12, 2013

(86) PCT No.: PCT/NZ2013/000140
§ 371 (c)(1),
(2) Date: Feb. 10, 2015

(87) PCT Pub. No.: WO2014/027897
PCT Pub. Date: Feb. 20, 2014

(65) Prior Publication Data
US 2015/0230941 A1    Aug. 20, 2015

Related U.S. Application Data

(60) Provisional application No. 61/682,291, filed on Aug. 12, 2012.

(51) Int. Cl.
*A61F 2/54* (2006.01)
*A61F 2/70* (2006.01)
(Continued)

(52) U.S. Cl.
CPC ............. *A61F 2/583* (2013.01); *A61F 2/586* (2013.01); *B25J 15/0009* (2013.01);
(Continued)

(58) Field of Classification Search
CPC .. A61F 2/586; A61F 2002/587; B25J 15/0009
(Continued)

(56) References Cited

U.S. PATENT DOCUMENTS 3,694,021 A    9/1972  Mullen
5,967,580 A *  10/1999 Rosheim ................... B25J 3/04
                                                       294/106
(Continued)

FOREIGN PATENT DOCUMENTS

CN       202572400 U    12/2012
FR       2 277 569 A2 *  2/1976  ............. A61F 2/586
(Continued)

OTHER PUBLICATIONS

International Search Report for PCT/NZ2013/000140 dated Dec. 6, 2013.

*Primary Examiner* — David H Willse
(74) *Attorney, Agent, or Firm* — Merchant & Gould P.C.

(57) ABSTRACT

The invention relates to a gripping device, such as an automated hand, comprising a plurality of metacarpal members, each metacarpal member having a first end attached to a support frame via a universal joint and having a second end attached to a gripping member, wherein the metacarpal members are able to pivot upwardly, downwardly and laterally. Where adjacent metacarpal members together form a palm of the hand, the ability of the metacarpal members to move up, down and laterally helps the palm to grip an object and also helps the palm to withstand at least some forces from above, below and from the side.

19 Claims, 20 Drawing Sheets

(51) Int. Cl.
 *A61F 2/58* (2006.01)
 *B25J 15/00* (2006.01)
 *A61F 2/50* (2006.01)

(52) U.S. Cl.
 CPC ......... *A61F 2002/5007* (2013.01); *A61F 2002/5038* (2013.01); *A61F 2002/5079* (2013.01); *A61F 2002/587* (2013.01); *A61F 2002/701* (2013.01)

(58) Field of Classification Search
 USPC .................................................... 623/63–64
 See application file for complete search history.

(56) References Cited

U.S. PATENT DOCUMENTS

| 2007/0040400 A1 | 2/2007 | Greenhill et al. |
| 2010/0176615 A1 | 7/2010 | Okuda et al. |
| 2010/0259057 A1 | 10/2010 | Madhani |
| 2011/0144770 A1 | 6/2011 | Moyer et al. |

FOREIGN PATENT DOCUMENTS

| GB | 151758 A | | 10/1920 | |
| JP | 2008-032140 A | * | 2/2008 | ............. B25J 15/08 |
| JP | 2012-192496 A | * | 10/2012 | ............. B25J 15/08 |

* cited by examiner

GRIPPING DEVICE

CROSS REFERENCE TO RELATED APPLICATIONS

This application is a National Stage of International Application No. PCT/NZ2013/000140 filed Aug. 12, 2013, claiming priority based on U.S. Provisional Application No. 61/682,291 filed Aug. 12, 2012, the contents of all of which are incorporated herein by reference in their entirety.

FIELD

The present invention relates to a gripping device, such as an automated hand for use as a prosthetic or robotic hand.

BACKGROUND

Gripping devices in the form of automated hands are known in the fields of prosthetics and robotics.

Many automated hands comprise a 'palm' and a plurality of gripping members or 'fingers'. The fingers of the hand are adapted to move so that objects can be gripped between the fingers.

United States patent publication no. US 2010/0259057 discloses a robotic hand with human-like fingers that are able to curl and flex using a series of pulleys and cables. United States patent application publication no. US 2011/0144770 discloses an automated finger mechanism for an automated hand. The fingers are able to curl and flex using differential linkages. However, in both forms of automated hand, the palm of the hand is fixed and does not comprise moveable portions and the fingers are not able to move laterally. This makes it very difficult for the hand to effectively and safely grip an object.

United States patent publication no. US 2010/0176615 discloses a multi-fingered robotic hand comprising a plurality of gripping members in the form of fingers and a thumb. Each of the fingers and thumb comprise hinged joints to allow the fingers and thumb to curl and flex. The robotic hand described has a palm comprising at least two palm portions attached together along an elongate hinged joint. The fingers and thumb extend from the palm of the hand in the direction of the y-axis. Metacarpal hinged joints between the fingers and the palm of the hand imitate the metacarpal joints of a human hand. The metacarpal hinged joints lie along the x-axis, which is perpendicular to the longitudinal direction of the fingers. These metacarpal hinged joints allow the fingers to pivot about the x-axis in a similar way as metacarpal joints allow human fingers to move relative to the palm of the human hand.

The elongate hinged joint connecting the two palm portions together is located along a second axis that is parallel to the x-axis of the metacarpal hinged joints of the fingers. The elongate hinged joint allows a first palm portion to move relative to a second palm portion so that the connection angle between the two palm portions can be varied to provide a compliant palm. The compliant palm therefore acts as an extension of the fingers by allowing the fingers and palm of the hand to curl and flex in the same way. However, the palm of the hand is unable to move about an axis that lies parallel to the y-axis or, in other words, neither the fingers of the hand nor the palm of the hand allow for lateral movement. Therefore, the palm of the hand can bend around an object in one direction only.

Contrast this with the human fingers, thumb, and palm, in which the metacarpal bones can move independently to some extent to bring the sides of the palm toward each other and in which the fingers and thumb can also move sideways to some extent. This movement, together with the curling and flexing abilities of the fingers and thumb allows the hand to grip an object very effectively, particularly a rounded or curved object, which can be 'cupped' by the hand.

Another drawback of known automated hands is that the fingers of the hand are particularly vulnerable to impacts from lateral forces. Furthermore, known automated hands typically appear bulky and look and feel unnatural.

It is an object of the invention to provide an automated hand comprising a compliant palm that goes at least some way towards overcoming or ameliorating one or more disadvantages of the prior art or that at least provides the public with a useful alternative.

SUMMARY OF INVENTION

In one aspect, the invention provides an automated hand comprising: a plurality of metacarpal members, each comprising a first end attached to a support frame via a universal joint and a substantially opposing second end attached to a gripping member, wherein the metacarpal members are adapted to pivot about the universal joint upwardly, downwardly, and laterally.

Preferably, each metacarpal member comprises a stabiliser having a first end attached to the support frame and a second end rotationally attached to a respective gripping member via a hinged joint, the stabiliser being springloaded to a neutral rest position and adapted to flex upwardly, downwardly, and laterally. Each stabiliser optionally attaches to a respective gripping member via a knuckle connector that angles the gripping member away from the stabiliser.

Preferably, at least two stabilisers form part of a metacarpal bracket having a base portion from which the stabilisers project and wherein the stabilisers are attached to the support frame via the base portion of the metacarpal bracket. Alternatively, or additionally, a flexible brace extends across and is attached to the stabilisers.

Preferably, each metacarpal member comprises an actuator having a first end attached to the support frame via the universal joint and a second end attached to a respective gripping member via a hinged transfer joint, wherein the actuator is adapted to linearly extend and retract to cause the respective gripping member to pivot about the transfer joint. In a preferred form, the actuator comprises an actuator arm and a drive system that engages with the actuator arm to cause the actuator arm to extend toward the gripping member and to retract away from the gripping member.

Optionally, a single actuator controls movement of at least one adjacent gripping member. In this form, a transfer arm may be operably attached to a first gripping member comprising an actuator and is also attached to a second gripping member to transfer movement of the first gripping member to the second gripping member and wherein the second gripping member is adapted to slide laterally along the transfer arm.

Preferably, the gripping members comprise a plurality of gripping portions corresponding to a proximal phalanx, a middle phalanx, and a distal phalanx, wherein each metacarpal member is attached to the proximal phalanx of a respective gripping member and wherein the proximal phalanx comprises a parallel linkage adapted to control movement of the proximal phalanx and of an adjacent phalanx upon actuation of the actuator.

Optionally, a plurality of adjacent metacarpal members form a palm.

Optionally, at least one gripping member is a thumb being positioned on the hand to substantially oppose at least one other gripping member. Preferably, the metacarpal member of the thumb is rotationally attached to a swiveling mounting block via a hinged joint, wherein the swiveling mounting block is rotationally attached to the support frame so that the mounting block forms the universal joint by which the metacarpal member of the thumb is attached to the support frame.

Preferably, the gripping members are adapted to move upwardly, downwardly, and laterally.

Preferably, the hand is for use as a prosthetic. Alternatively, the hand is for use as a robotic hand.

In another aspect, the invention comprises an automated hand comprising: a palm portion formed from a plurality of metacarpal members, wherein one end of each metacarpal member is hingedly attached to a support via a universal joint and an opposing end of each metacarpal member is attached to a respective gripping member, and wherein two or more metacarpal members are able to independently pivot up, down, and laterally about the support.

Preferably, the metacarpal members each comprise a flexible stabiliser and an actuator, the actuator being adapted to extend and retract in a linear direction, wherein one end of the actuator is attached to the support via the universal joint.

More preferably, each stabiliser is attached to a respective gripping member and each actuator is attached to the respective gripping member via a metacarpophalangeal joint and wherein the gripping members are able to pivot up and down relative to the metacarpal members via the metacarpophalangeal joint.

The metacarpophalangeal joint is optionally attached to a parallel linkage forming a proximal phalanx of the gripping member, the parallel linkage being adapted to control movement of the proximal phalanx and to control movement of an adjacent phalanx of the gripping member upon actuation of the actuator.

Preferably, the hand comprises four gripping members in the form of fingers and a substantially opposing gripping member forming a thumb. Optionally, the gripping members in the form of fingers each have a first gripping portion corresponding to the proximal phalanx, a second gripping portion corresponding to a middle phalanx and a third gripping portion corresponding to a distal phalanx.

The gripping members may comprise one or more gripping portions that are curved, angled or straight.

In one form, one or more gripping members of the hand comprise a gripping portion that is curved downwardly.

In one form, the distal phalanx is attached to the middle phalanx so that the distal and middle phalanges can move simultaneously. Optionally, the distal phalanx is attached to the middle phalanx via a link so that both the middle phalanx and distal phalanx can move independently of each other.

Preferably, the actuator comprises a telescopically extending actuator arm, a housing, and a drive system, that causes the actuator arm to retract within the housing and to extend from the housing upon receiving an actuation signal from a control system.

Preferably, at least one gripping member comprises a proximal phalanx comprising a parallel linkage having first and second links each having first and second ends, wherein the first end of the first link is rotationally attached to a respective stabiliser via a connector so that the first link can pivot vertically about the connector and wherein a first end of the second link is rotationally attached to a respective actuator arm so that the second link can pivot vertically about the actuator arm, wherein the second ends of the first and second links are rotationally attached to an adjacent phalanx to allow the adjacent phalanx and parallel linkage to pivot independently, and wherein the parallel linkage also comprises third and fourth links, the third link attaching the first and second links together, and the fourth link providing a spacer link that connects the second link to the actuator arm.

In one form, at least two gripping members are controlled by a simultaneous movement actuation system adapted to allow the two members to move simultaneously.

Preferably, the simultaneous movement actuation system comprises a guide rail extending along the length of the actuator housing of a control finger, a sliding frame adapted to slide along the guide rail, at least one connector arm, having a first end attached to the sliding frame and having a second end rotationally attached to the distal end of the actuator arm of the control finger, wherein the connector arm is also attached to a first end of a transfer arm, the second end of the transfer arm being rotationally attached to the gripping member of a subsidiary finger so that movement of the actuator arm of the control finger causes simultaneous movement of the subsidiary finger.

Optionally, the control finger comprises two connector arms, one on each side of the control finger.

In one form, the automated hand comprises a plurality of metacarpal members forming a palm and at least one gripping member corresponding to a thumb and positioned on the palm of the hand to substantially oppose at least one other gripping member. Optionally, the thumb extends from the palm of the hand to make an angle with the palm of substantially between 20 and 70 degrees.

Preferably, the thumb is rotationally mounted on a rotating angular base to allow the thumb to pivot toward and away from a central region of the palm of the hand and also allowing the thumb to move laterally in an arc.

More preferably, the thumb comprises a single gripping portion that is rotationally attached to the stabiliser of the thumb via a respective knuckle connector and is also attached to the actuator.

In one form of automated hand according to the invention, two or more stabilisers are joined together by a flexible brace, extending across first or second surfaces of the stabilisers.

Preferably, each gripping member is attached to a respective stabiliser via a knuckle connector, wherein the knuckle connectors are shaped to simulate the external appearance of human knuckles.

In a preferred form, the stabilisers are made of spring steel.

Preferably, one or more gripping portions of the gripping members comprise textured or tacky contact surfaces to assist the hand to grip an object.

Preferably, the hand is covered by a stretchy covering, membrane, or skin.

In another aspect, the invention comprises a thumb for an automated hand, the thumb being attached to a swiveling mounting block via a hinged joint to allow the thumb to pivot up and down, and the swiveling mounting block being rotationally attached to a support frame to allow the mounting block to swivel so that the thumb moves laterally.

Preferably, the thumb and swiveling mounting block are adapted so that the thumb is mounted on an angle to the support frame.

Preferably, the thumb comprises a metacarpal member comprising a flexible stabiliser and an actuator, and further comprises a gripping portion rotationally attached to the metacarpal member such that the actuator causes the gripping portion to pivot up and down.

The term "comprising" as used in this specification and claims means "consisting at least in part of". When interpreting each statement and claim in the specification that includes the term "comprising", features other than that or those prefaced by the term may also be present. Related terms such as "comprise" and "comprises" are to be interpreted in the same manner.

The term "universal joint" refers to any joint between two members that allows at least one of the two members to pivot up, down and laterally about the joint.

The term "downwardly" refers to movement in the direction in which the contact surfaces of the gripping members face (the contact surfaces being those surfaces that contact an object gripped by the hand). Conversely, the term "upwardly" as used in the specification and claims refers to movement in the direction in which the upper surfaces of the gripping members face (the upper surfaces being those surfaces opposite the contact surfaces and that correspond to the backs of the fingers and thumb of a human hand).

Any discussion of the prior art throughout the specification should in no way be considered as an admission that such prior art is widely known or forms part of common general knowledge in the field.

The invention consists in the foregoing and also envisages constructions of which the following gives examples only.

BRIEF DESCRIPTION OF THE DRAWINGS

FIG. 18a is a top view of the sliding frame of the simultaneous movement actuation system of FIG. 18;

FIG. 18b is a rear view of the sliding frame of the simultaneous movement actuation system of FIG. 18;

DETAILED DESCRIPTION

In each embodiment of the invention described, the automated hand is described and shown as if it is oriented so that contact surfaces of the hand (being those surfaces of the gripping members and metacarpal members that contact an object gripped by the hand) face downwardly toward the ground. By way of analogy, the automated hand is shown orientated in the same manner as a person standing upright would hold their hand out with palm facing down.

In one form, the invention relates to an automated hand, for use as a prosthetic hand or robotic hand. The automated hand comprises a support frame (where the hand attaches to a wrist portion), to which is attached a plurality of metacarpal members that are attached to a plurality of movable gripping members.

Each of the metacarpal members have a first end attached to the support frame (located at the base of the hand) via a universal joint. Each metacarpal member also has an opposing second end attached to a respective gripping member (in the form of a finger or thumb). The metacarpal members are similar in function to the metacarpal bones of the human hand and are adapted to move up and down and laterally. In this way, the metacarpal members are able to move between a closed gripping position and an open release position and can also move laterally.

The movable gripping members of the hand can also move up, down, curl, and flex to move between a closed gripping position (in which the gripping members curl) and an open release position in which the fingers flex and extend. The gripping members can also move laterally to some extent. Typically, the automated hand comprises at least two gripping members, one gripping member in the form of a finger and a substantially opposing gripping member forming a thumb.

At least two adjacent metacarpal members may together form a palm of the hand.

The ability of the metacarpal members and gripping members (fingers and thumb) to move laterally allows the hand to feel softer, more compliant, and natural when it is gripped in a handshake, for example. It also allows the hand to withstand, to at least some extent, impact forces hitting the hand from above, below, and from the side. In addition, the hand is able to substantially conform around an object held by the hand.

Figure 1:
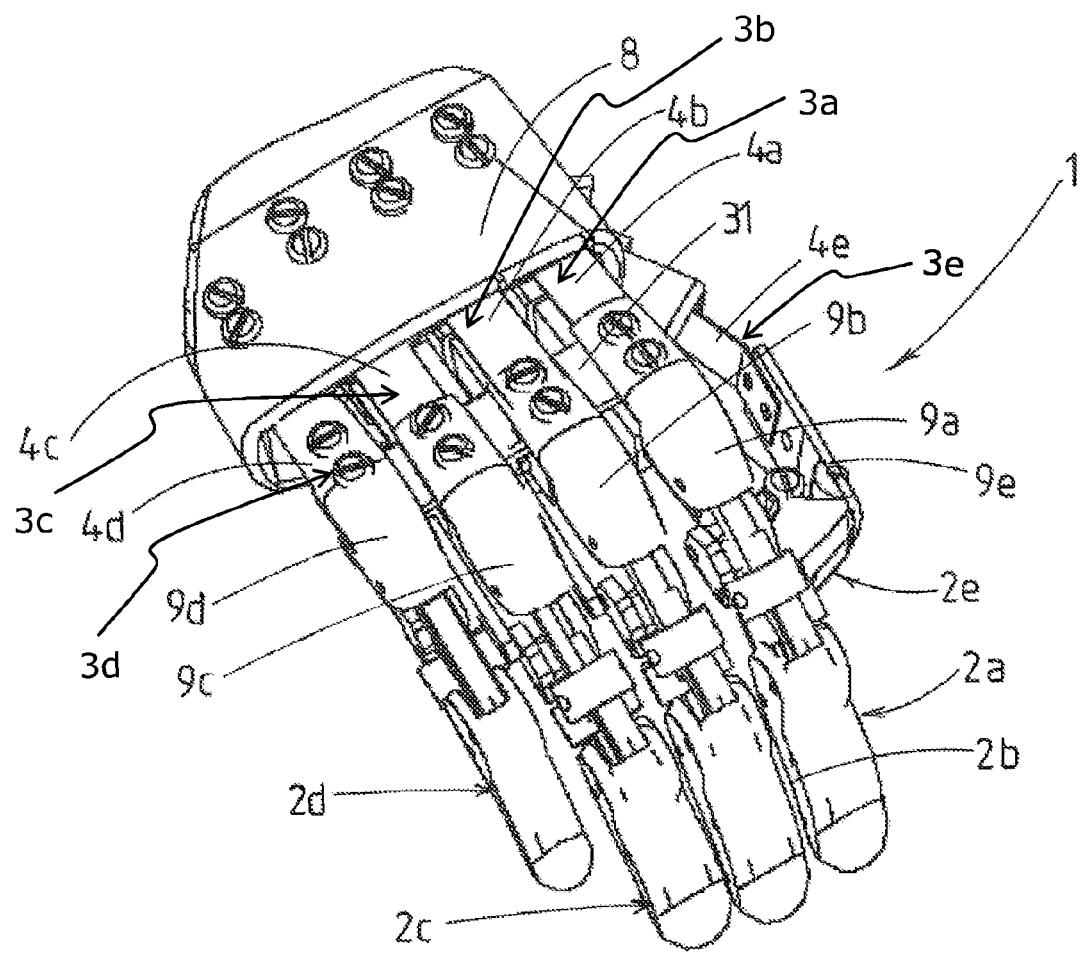
FIG. 1 is a perspective view from above of a gripping device in the form an automated hand according to the present invention.

FIG. 1 illustrates one form of the invention in which the automated hand 1 comprises a plurality of gripping members 2a-2e, each extending from a respective metacarpal member 3a-3e, as described above. Four of the gripping members 2a-2d are in the form of fingers attached to four metacarpal members 3a, 3b, 3c, 3d that form the palm of the automated hand 1. The metacarpal members 3a-3d are rotationally attached to a support frame 8 via a universal joint, so that the metacarpal members are able to pivot up and down between an open release position and a closed gripping position. The metacarpal members are also able to pivot laterally. The support frame 8 is located at the base of the hand and is part of a lower wrist portion for fitting on a user's arm. The full wrist portion is not illustrated. The automated hand also comprises a gripping member in the form of a thumb 2e that substantially opposes at least one other gripping member. The gripping member of the thumb is attached to a metacarpal member 3e that is rotationally attached to the support frame 8 so that the thumb can pivot between an open and closed position and can also pivot laterally.

As shown best in FIGS. 1 to 5a, each metacarpal member comprises a flexible, resilient stabiliser 4a-4e that is springloaded (biased) to a neutral, rest position. The stabilisers provide a degree of stability to the metacarpal members of the hand, but allow for at least some upward and downward flex, lateral movement, and twist. Each stabiliser also provides the respective metacarpal member with a substantially stable connection point at which a respective gripping member is attached to the stabiliser.

The stabilisers each comprise an elongate, resilient body in the form of a rod, plate, or the like having first and second ends, a first surface and a second surface. The first surfaces of the stabilisers also form the first surfaces of the metacarpal members. The first surfaces of adjacent finger stabilisers 4a-4d (being the stabilisers attached to gripping members corresponding to the fingers of the hand) form the back of the palm of the hand.

Figure 5:
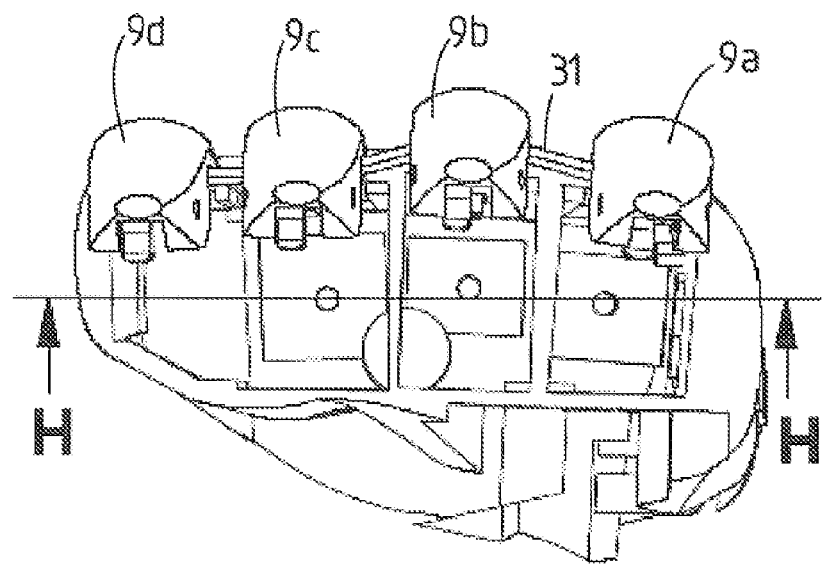
FIG. 5 is a front view of part of a hand according to one form of the invention and in which the fingers are partially spread.
Figure 5A:
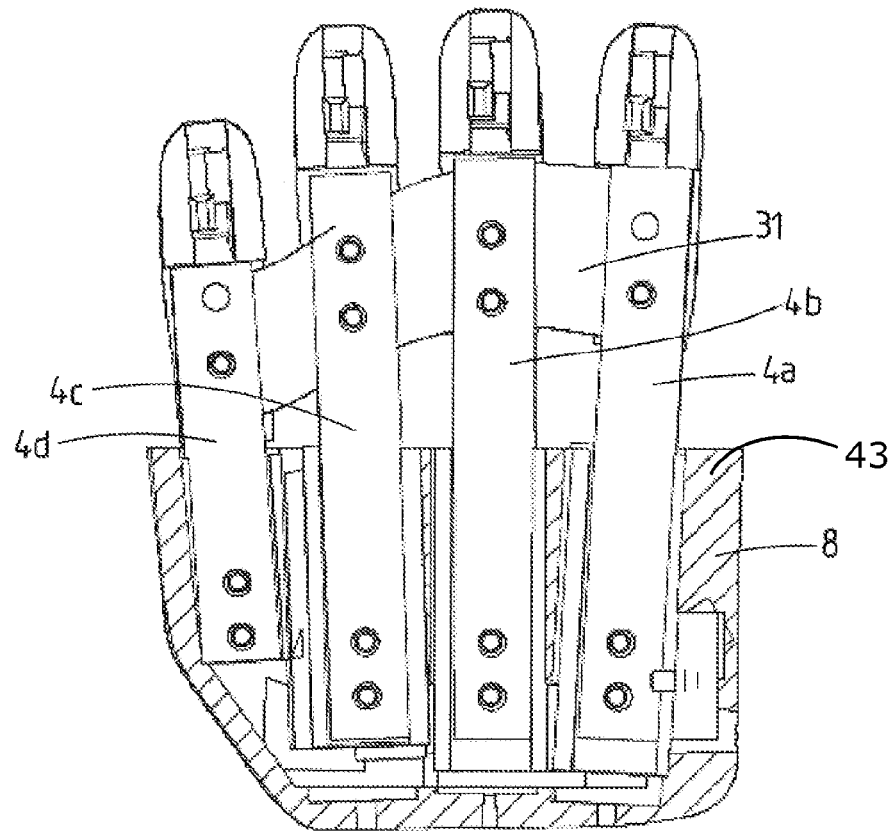
FIG. 5a is a cross-sectional view of the hand of FIG. 5 taken along line H-H.
Figure 6:
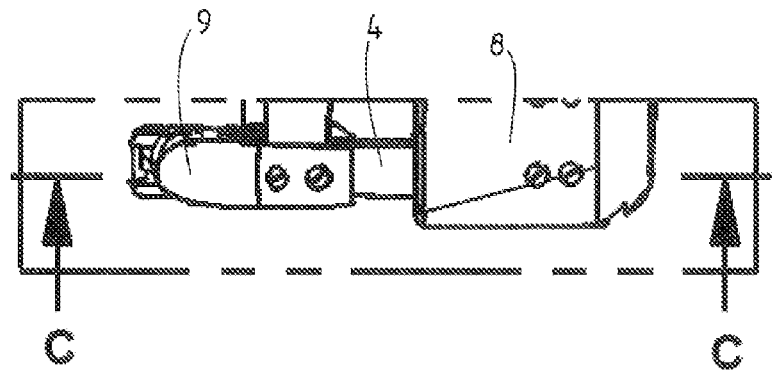
FIG. 6 is a top view of a finger in a partially curled position according to one form of the invention.

Each stabiliser is attached to the support frame 8 at the base of the hand and is adapted to flex up and down. The stabilisers are also able to flex laterally to some extent, as shown in FIGS. 5 and 5a. So, the flexible stabilisers provide the metacarpal members with upward and downward flexion, lateral flexion and twist flexion to some extent.

The stabilisers are made of a flexible, resilient, but strong material, such as spring steel, polypropylene or, polystyrenes (un-expanded), or PVC.

In one form, the first end of each stabiliser is individually attached to the support frame, as shown in FIGS. 1, 2, 5, and 5a.

Figure 3:
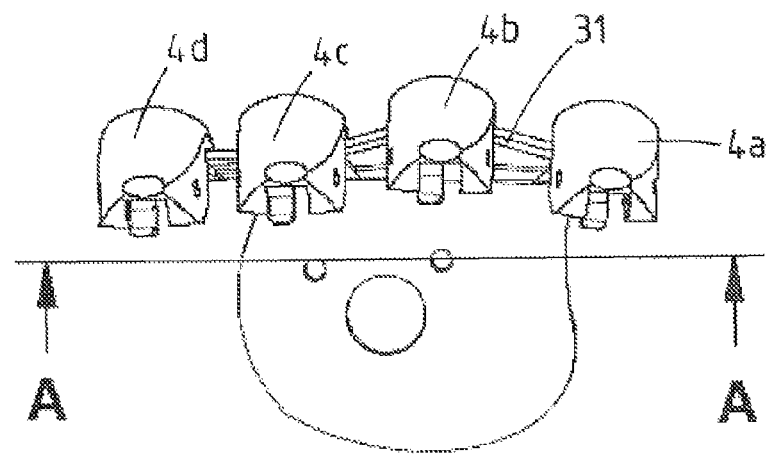
FIG. 3 is an end view of the finger stabilisers and flexible brace according to one form of the invention.
Figure 3A:
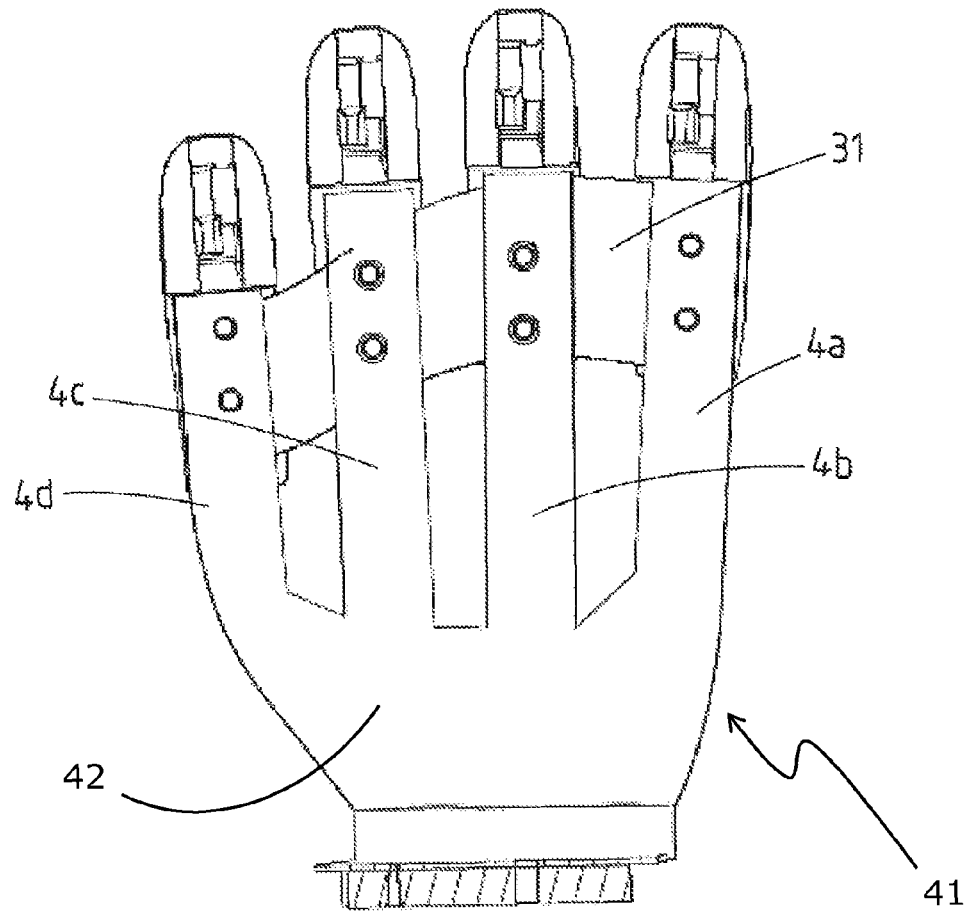
FIG. 3a is a cross-sectional view taken along line A-A of FIG. 3.
Figure 4:
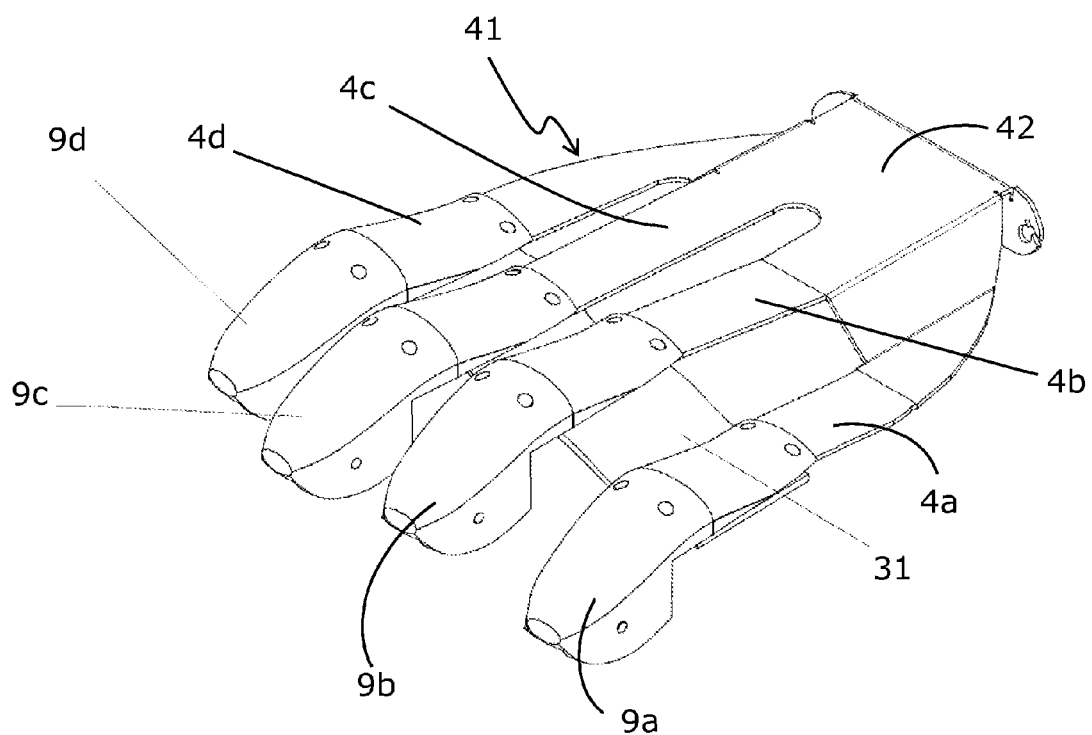
FIG. 4 is a perspective view from above of the metacarpal bracket according to one form of the invention.

Alternatively, at least two finger stabilisers 4a-4d may form part of a stabilising metacarpal bracket 41, as shown in FIGS. 3, 3a, and 4. The metacarpal bracket 41 is formed of a flexible, resilient material (such as spring steel) and comprises a base portion 42 from which each of the stabilisers 4a-4d project in a fork-like arrangement. The base portion 42 of the metacarpal bracket 41 is attached to the support frame 8 at the base of the hand, so that the finger stabilisers 4 are attached to the support frame via the base portion. Typically, the stabilisers are integral with the base portion of the metacarpal bracket to form a single part. The thumb stabiliser 4e is individually attached to the support frame 8.

The stabilising metacarpal bracket 41 may be anatomically matched to a human hand by comprising an upper surface that curves or angles toward the palm of the hand, as shown in FIG. 4.

In one form, as shown in FIGS. 1 to 5a, the finger stabilisers 4a-4d are attached to each other via support means in the form of a flexible brace 31, which spans across and is attached to the finger stabilisers. The flexible brace may span across and be attached to either the first or second surfaces of the finger stabilisers.

The flexible brace 31 allows the metacarpal members 3a-3d of the fingers to move independently relative to each other to some extent to provide a compliant palm, as described above, whilst still retaining the structural integrity of the palm and helping to prevent straining or damage to the metacarpal members or component parts of the hand. In particular, the flexible brace 31 helps to restrict twisting of the metacarpal members 3 under torsional forces and helps to prevent the metacarpal members from moving too far apart from each other. In this way, the flexible brace provides the palm of the hand with added strength, stability, and security from damage. This is because a significant separation of the metacarpal members is likely to weaken the hand and may also expose the individual metacarpal members to a greater risk of damage if one or more metacarpal members is/are impacted by an external force.

In yet another form, the lateral movement of the metacarpal members is alternatively or additionally limited by a funicular collar 43 that extends from the support frame 8 and surrounds at least a portion of the metacarpal members 3 proximate to the support frame, as shown in FIG. 5a. The funicular collar may be attached to or integral with the support frame.

Alternatively, the metacarpal members (and the rest of the hand) may be supported or braced by being covered in a skin, membrane, or other covering that stretches to allow the metacarpal members to move up, down, and laterally, but that limits the extent of lateral movement and twist of the metacarpal members.

Figure 2:
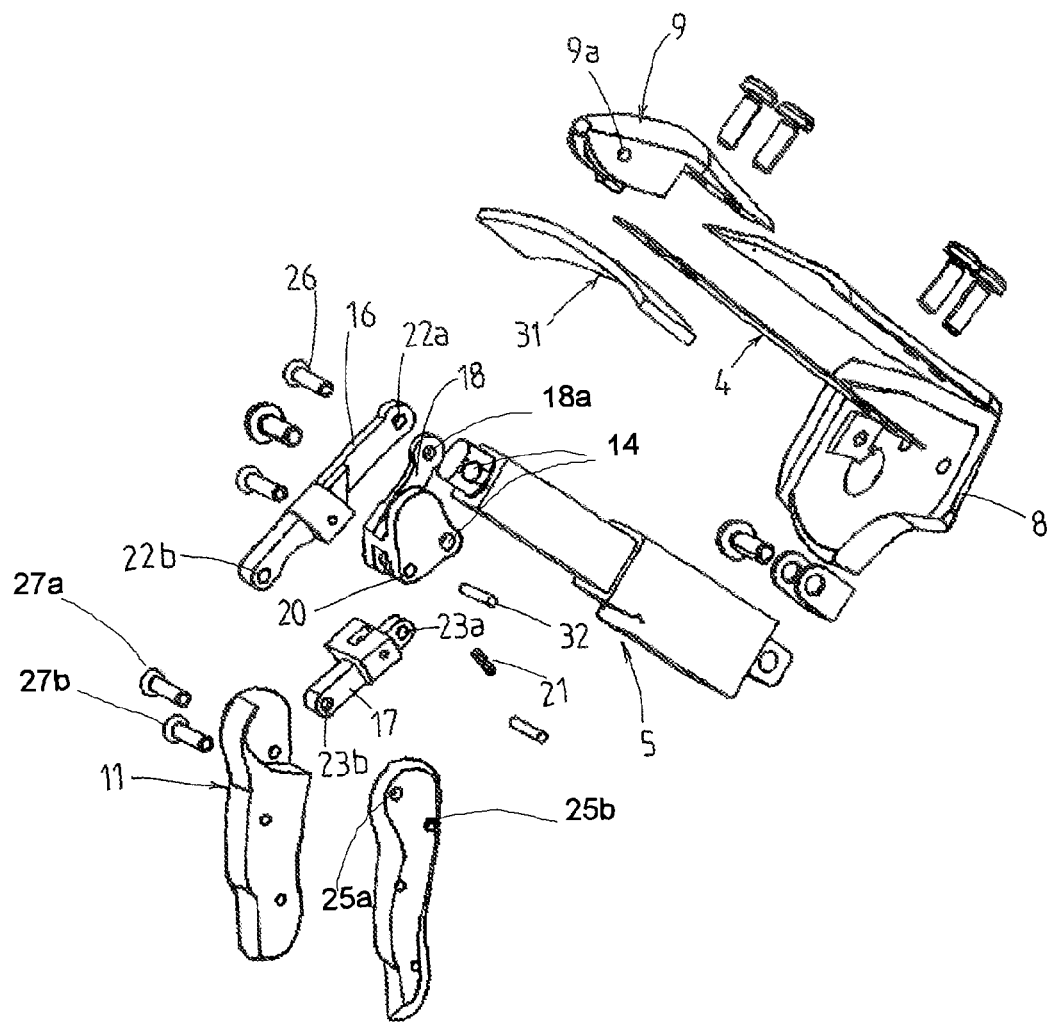
FIG. 2 is an exploded view of a finger and metacarpal member of the hand shown in FIG. 1.

Each metacarpal member 4a-4e is attached to a respective gripping member 2a-2e. In one form, the second end of each stabiliser of a metacarpal member attaches to a respective gripping member via a knuckle connector 9, as shown in FIGS. 4 to 16. The knuckle connector may be integral with the body of the stabiliser so that the knuckle connector and stabiliser are formed as a single part, such as by co-moulding. Alternatively, the knuckle connector may be formed as a separate part that is attached to the stabiliser by welds, screws, rivets, adhesive, or other suitable attachment means, as shown in FIG. 4.

Where the knuckle connector is integral with the stabiliser, the knuckle connector may form a widened and/or thickened second end of the stabiliser, to provide a larger surface area by which the gripping member can attach to the stabiliser in a suitably stable joint. For example, the stabiliser may comprise an enlarged, downwardly curved knuckle connector at its second end, the knuckle connector preferably being shaped to simulate a human knuckle.

Where the knuckle connector is a separate part attached to the stabiliser body, as shown in FIGS. 1, 2, and 4, the knuckle connector may optionally be formed to provide a sufficient surface area so that the gripping member and stabiliser can attach to each other via a stable joint. To provide sufficient stability to the joint and to enhance the aesthetic appeal of the hand, the knuckle connector is preferably shaped to have an angled or curved profile to substantially simulate the form of a human knuckle.

Figure 20:
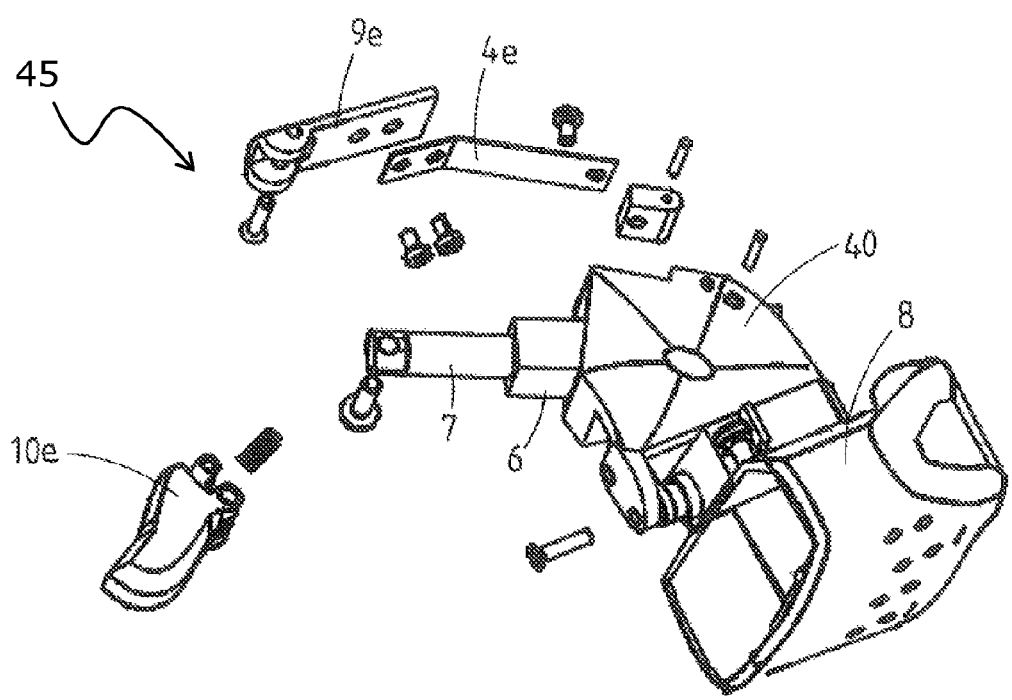
FIG. 20 is an exploded view of thumb components according to one form of the invention.
Figure 21:
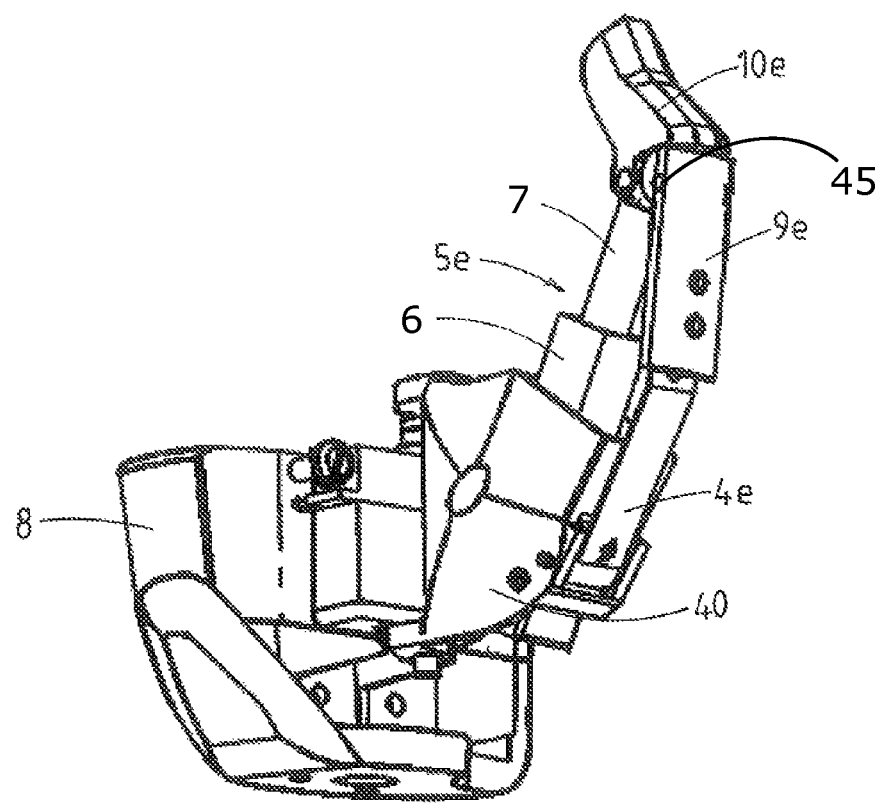
FIG. 21 is a perspective view of the assembled thumb of FIG. 20 attached to a support frame.

For example, as shown in FIGS. 20 and 21, each knuckle connector may be an elongate plate attached to an angled stabiliser, the stabiliser being angled downwardly to simulate both a metacarpal bone and a proximal phalanx of a human hand in which, in a neutral rest position, the proximal phalanx angles slightly downwardly from the back of the hand.

The knuckle connectors 9 attach gripping members 2 to the stabilisers 4 via a hinged joint 45, allowing the gripping members to pivot up and down about the hinged joint 45. Each knuckle connector has an attachment end that provides a hinged joint to which the gripping member is attached. For example, as shown in FIGS. 20 to 23, the attachment end may be substantially U-shaped, having an aperture located in each side of the arms of the U. The apertures are aligned with each other and also align with one or more apertures on the gripping member. A pivot shaft is located between the aligned apertures so that the gripping member can pivot up and down about the shaft.

Optionally, the stabiliser, knuckle connector and gripping member are adapted so that the gripping member attaches to the stabiliser via the knuckle connector and so that the gripping member is angled downwardly from the first surface of the stabiliser, as shown in FIGS. 4, 8 to 16, 20, and 21.

Figure 8:
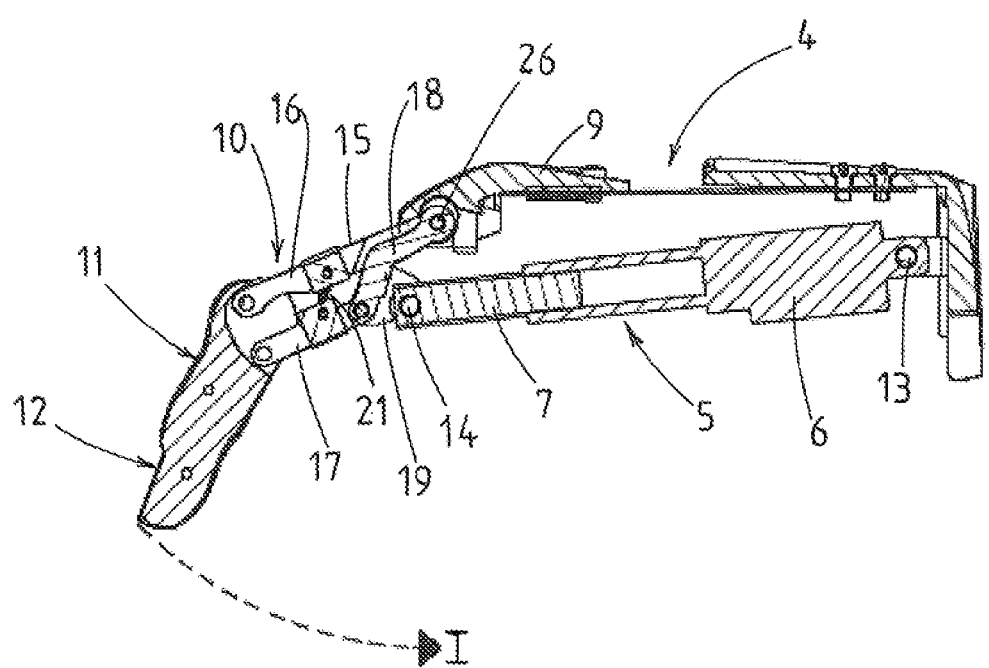
FIG. 8 is a cross-sectional side view of a finger taken along line B-B of FIG. 6 and in which the finger is partially extended.
Figure 9:
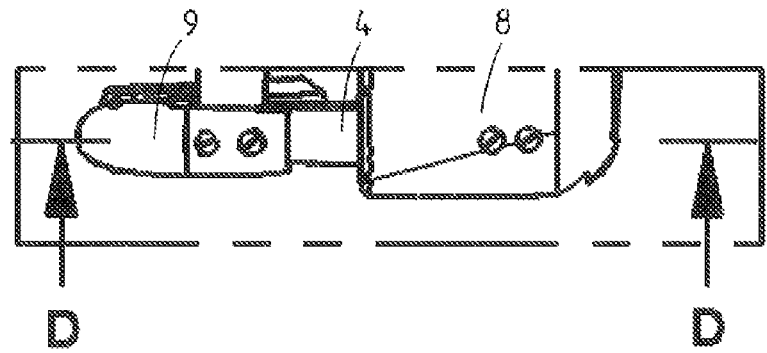
FIG. 9 is a top view of a finger in a curled position according to one form of the invention.
Figure 10:
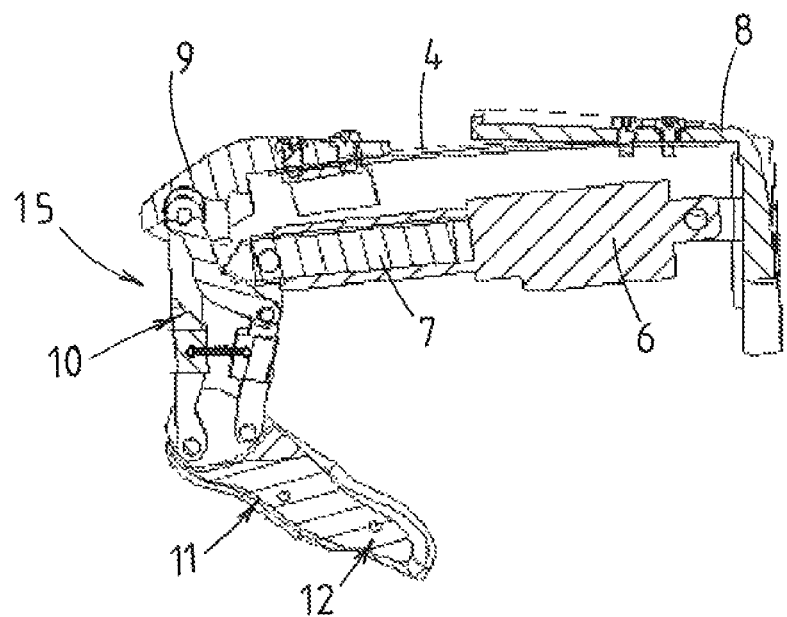
FIG. 10 is a cross-sectional view of a finger taken along line D-D of FIG. 9.
Figure 11:
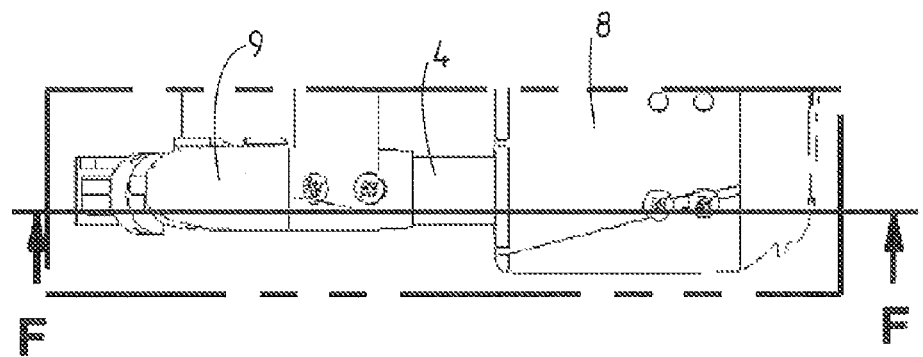
FIG. 11 is a top view of another form of finger according to the invention.

By attaching the gripping members to the stabilisers in an angular arrangement, the neutral rest position of the hand simulates the appearance of a relaxed human hand in which the fingers and thumb are slightly curled downwardly, as shown in FIGS. 8 and 21. For example, when the human hand is in a neutral, relaxed position, the fingers and thumb of the hand are not fully flexed, so an automated hand that assumed such a neutral position would look unnatural. The angled or curved connection between the stabilisers and gripping members also reduces the extent to which the gripping members need to curl to grip an object and recognises that it is very seldom that the fingers of a hand need to be flexed to the extent that they align with the palm of the hand. However, it is not essential that each gripping member and stabiliser is attached in an angular arrangement. Each stabiliser could instead be attached to a gripping member so that when the respective gripping member is fully flexed, it lies substantially in the same plane as the stabiliser. Regardless of whether the gripping members are attached to the stabilisers in an angular arrangement or not, when a gripping member is fully flexed, it is under tension, which means that it can be used for pointing tasks such as typing.

The knuckle connector and the stabiliser may be formed of the same or different materials. The knuckle connector is optionally formed of plastic, wood, metal, spring steel or any other suitably solid and mouldable material and is fixed to the stabiliser, which is optionally formed from spring steel or plastic or any other suitably flexible and resilient material.

Each metacarpal member 3a-3e also comprises an actuator 5 for actuating movement of the gripping members 2a-2e, so that the gripping members can curl and flex.

Each actuator 5 comprises a linearly extending and retracting actuator arm having substantially opposing first and second ends. The actuators for fingers forming the palm of the hand provide the palm with a contact surface, which is the surface that will contact an object held within the palm.

Figure 24:
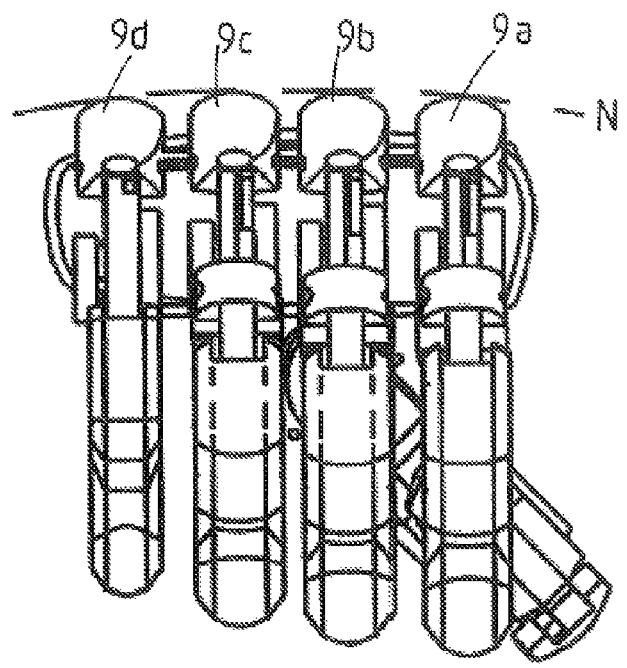
FIG. 24 is a front view of one form in which the metacarpal members of the fingers are in the neutral, rest position.
Figure 25:
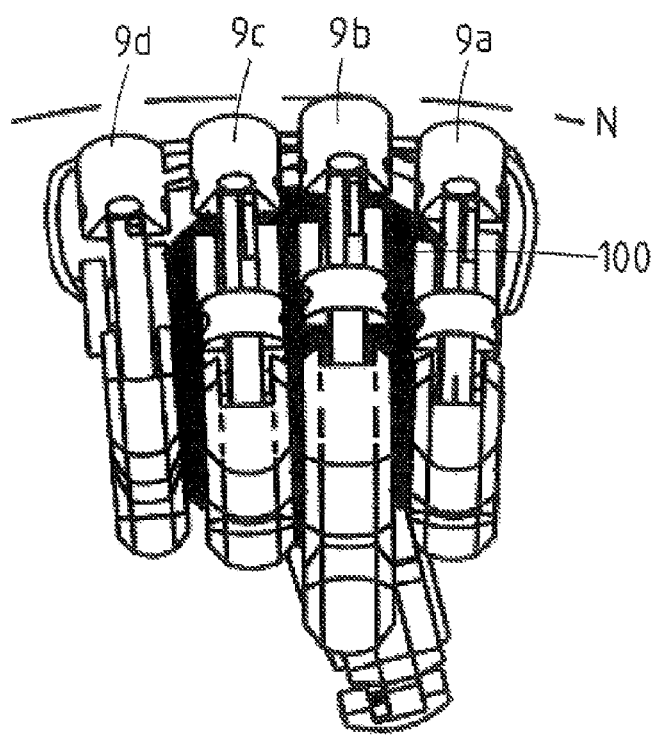
FIG. 25 is a front view of the hand shown in FIG. 24 in which the metacarpal members of the fingers have moved from the neutral position to a gripping position.

The first end of each actuator is attached to the support frame 8 at the base of the hand via a universal joint 13, as shown in FIGS. 2, 7, 8, 10, 12 14, 16, 18, 19, and 21 to 23, about which the actuator 5 can pivot up and down and laterally (side to side) to some extent. The universal joint allows the actuator arm to pivot up and down in a direction toward the stabiliser and away from the stabiliser respectively. The universal joint also allows the actuator arm to pivot laterally. The upward, downward, and lateral movement of each actuator causes the respective stabiliser to move in the same direction. Thus, the metacarpal members of the hand are independently able to pivot up, down, and laterally. In this form of the invention, where the metacarpal members of the fingers form the palm of the hand, the palm is compliant in the longitudinal direction, as shown in FIGS. 24 and 25, and in the lateral direction, as shown in FIGS. 5 and 5a. In this arrangement, when the hand is squeezed in a grip or when a lateral impact causes lateral flexion of a gripping member, the actuator can move in the direction of the lateral force so as not to strain the universal joint 13.

The second end of each actuator 5 (the distal end) is attached to a gripping member 2 via a transfer joint 14. The gripping member is also attached to a respective stabiliser 4, so that each actuator is indirectly attached to a respective stabiliser. Therefore, upward and downward movement of the actuator causes the stabiliser to move in the same direction so that the metacarpal members of the hand are independently able to pivot up and down.

The actuator is adapted to linearly extend and retract in a direction that substantially follows the longitudinal direction of the metacarpal members.

In one form, as shown in FIGS. 2, 7, 8, 10, 12, 14, 17, and 17a, the actuator 5 comprises a telescopically extending actuator arm 7, a housing 6, and a drive system.

The drive system is located within the housing together with a first end of the actuator arm. The second end of the actuator arm is attached to a gripping member via a transfer joint 14. The drive system comprises a motor and a drive means in the form of a threaded spindle 63, which is caused to rotate by the motor. The spindle can rotate clockwise or anti-clockwise depending on whether the actuator is required to extend or retract. The housing 6 comprises a hollow interior and has an opening 61 at one end through which the actuator arm 7 can extend. The actuator arm 7 is sized so that it can slide into the housing 6, through the housing opening 61, to reach a fully retracted position and so that it can slide out of the housing to reach a fully extended position. In the fully retracted position, at least the distal end of the actuator arm on which the transfer joint 14 is located remains projecting from the housing opening 61. When in the fully extended position, a collar 62 on the first end of the actuator arm contacts a stop (such as an annular flange or other projection) located on the interior of the housing opening 61 to prevent the actuator arm separating from the housing.

The first end of the actuator arm comprises a cylindrical threaded hollow interior, which is sized to receive at least a portion of the threaded spindle. The threaded spindle projects into the actuator housing and meshes with the hollow interior of the actuator arm to engage with the first end of the actuator arm. As the spindle rotates in one direction, the actuator arm moves along the spindle to extend from the housing. In this way, the length of the actuator is increased and the actuator arm pushes against the gripping member to cause the gripping member to flex. Conversely, when the spindle rotates in the opposite direction, the actuator arm moves along the spindle in a direction away from the gripping member, causing the actuator arm to substantially retract into the housing. The length of the actuator is caused to decrease so that the actuator arm pulls on the gripping member, causing the gripping member to curl.

In another form, the actuators are positioned on the hand in reverse orientation so that the distal end of each actuator arm is attached to the support frame via a universal joint and the respective gripping member is attached to the other end of the actuator via a transfer joint.

Figure 15:
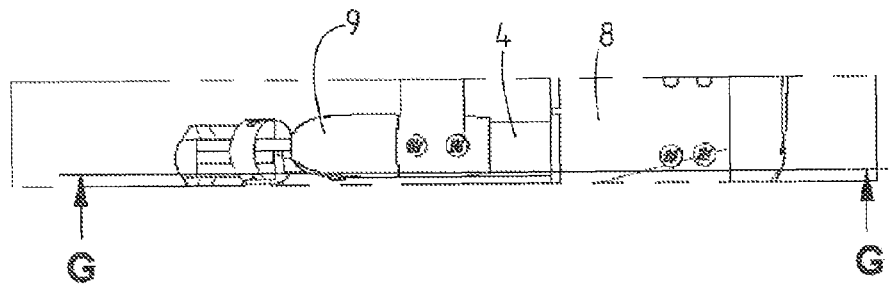
FIG. 15 is a top view of a finger according to another form of the invention.
Figure 16:
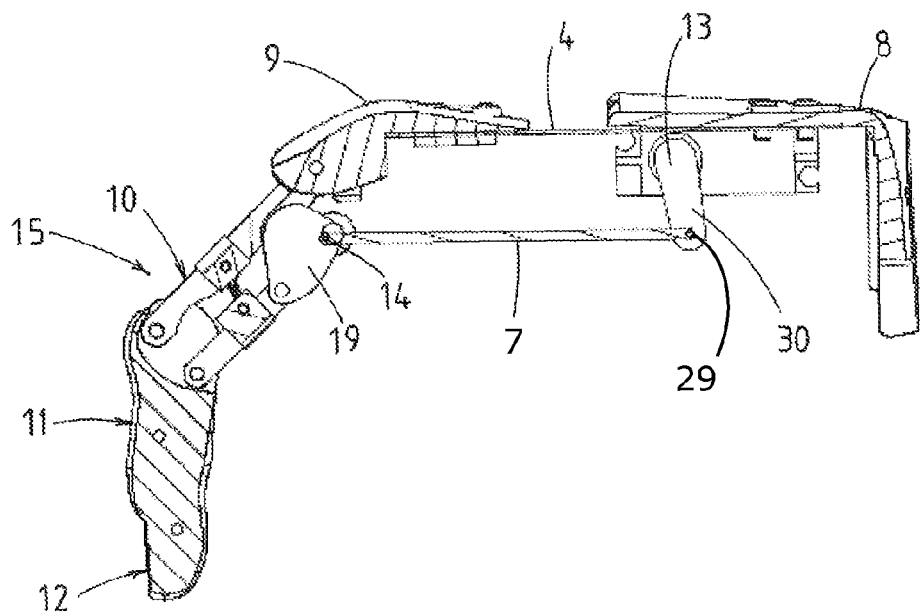
FIG. 16 is a cross-sectional view of the finger of FIG. 15 taken along line G-G.
Figure 17A:
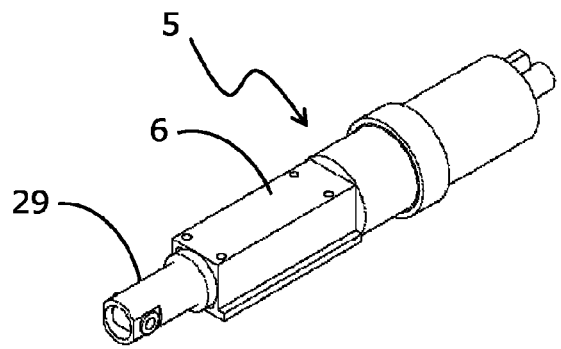
FIG. 17a is a perspective view of the assembled actuator of FIG. 17.
Figure 17:
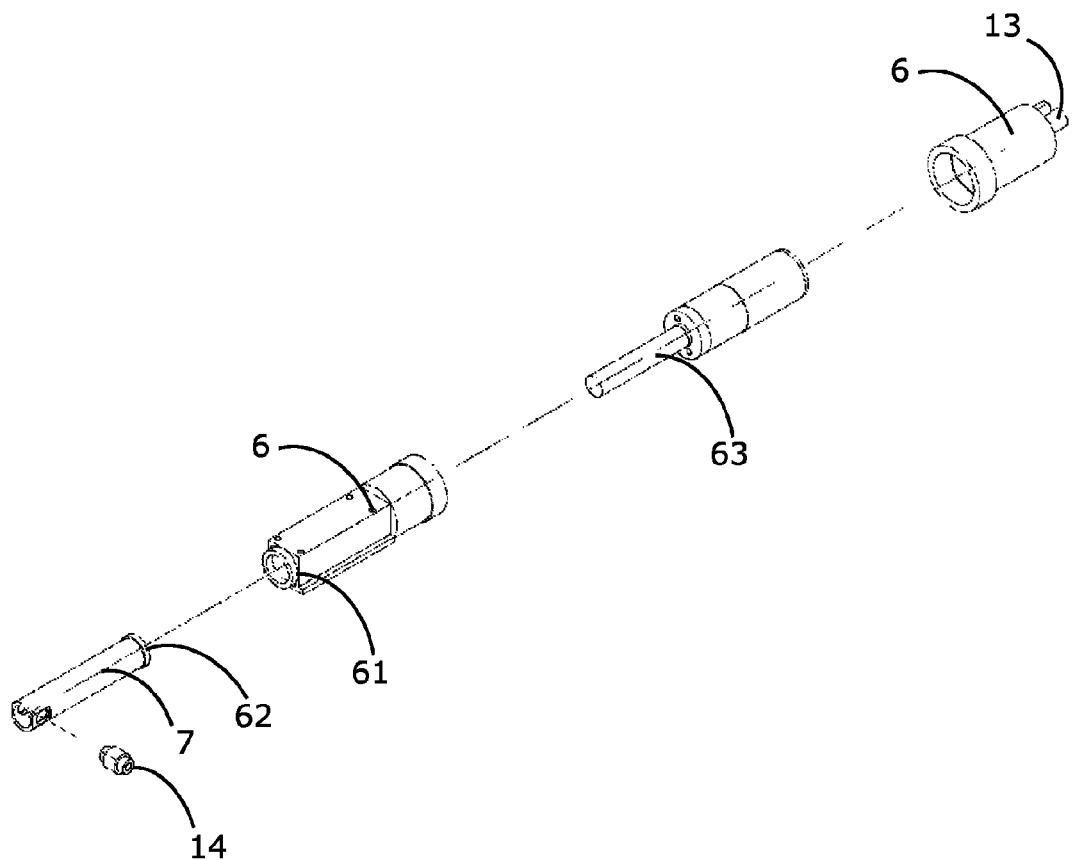
FIG. 17 is an exploded view of an actuator according to one form of the invention.

In another form, as shown in FIGS. 15 and 16, the actuator comprises an actuator arm, a housing, and a drive system, as described above. The drive system comprises a motor, which is located within the housing, and also comprises a drive means in the form of a rotating lever 30. One end of the rotating lever extends from the housing and is attached to the housing and motor via a pivot joint 13 such that the motor can cause the rotating lever to partially rotate up and down about the pivot joint 13. The actuator arm is adapted so that under lateral impact, the actuator will flex laterally, in a similar manner to a stabiliser. The distal end of the rotating lever 30 is attached to a first end of the actuator arm 7 via a hinged joint 29. The second end of the actuator arm is attached to a gripping member 2 via a transfer joint 14.

In this form, as the motor causes the rotating lever 30 to rotate toward the actuator arm 7, the actuator arm extends by being pushed toward the gripping member. Thus, the length of the actuator increases and the gripping member is caused to move upwardly and flex. Conversely, as the rotating lever 30 rotates away from the actuator arm 7, the actuator arm is caused to retract and pull away from the gripping member. The length of the actuator is consequently decreased and the gripping member is caused to curl.

Alternative forms of actuators that are adapted to increase and decrease in length in the longitudinal direction of the metacarpal members can otherwise be used without departing from the scope of the invention. For example, a telescopically or linearly extending and retracting piston-like actuator arm driven by hydraulics or air pressure may be used.

As mentioned above, the second end of each stabiliser is rotationally attached to the gripping member via a knuckle connector and the second end of each actuator arm is rotationally attached to a respective gripping member via a transfer joint. Each stabiliser and actuator together form a metacarpal member. The attachment between the gripping member and metacarpal member forms a metacarpophalangeal joint that allows linear retraction movement of the actuator to cause the gripping members (fingers and thumb) to curl to form a gripping position in which an object can be gripped. The joint also allows linear extension movement of the actuator to cause the gripping members to flex, so that the gripping members flex or straighten to form a release position in which an object can be released.

Thus, the actuator, together with the transfer joint for connecting the gripping members to the actuator, is adapted so that linear movement of the actuator creates rotational movement of at least a portion of the gripping member so that the gripping member can curl and flex.

Each gripping member has a contact surface that corresponds with the lower contact surfaces of human fingers and thumbs of a hand with a palm facing the ground. It is these contact surfaces that come into contact with an object being gripped by the automated hand. The contact surfaces may be substantially flat, stepped, tapered, curved, textured, or tacky to assist with gripping slippery or curved objects. Each gripping member also has an upper surface corresponding to the backs of the fingers and thumbs of human hands. As will be appreciated, the areas of the gripping member that form the contact surface and the areas that form the upper surface remain the same, regardless of the orientation of the hand.

Each gripping member comprises a plurality of gripping portions that are able to curl and grip an object. The gripping portions may be of any suitable form. For example, the gripping portions may be curved, angled, or straight. The gripping portions may be attached together in a fixed position, they may be integral with each other and formed as a single part, or they may be attached via joints that allow the gripping portions to pivot relative to each other so that the gripping portions can curl and flex.

In one form, one or more gripping members comprise a single gripping portion. In this form, the gripping portion forms a finger or thumb that is curved or angled downwardly from the support frame or palm of the hand to form a claw-like gripping member.

In a preferred form, one or more gripping members comprise a plurality of gripping portions in the form of segments that substantially correspond to the segments of the fingers and thumb of a human hand. For example, where the gripping member acts as a finger, the gripping portions comprise three segments corresponding to a proximal phalanx, middle phalanx, and distal phalanx. Where the gripping member is a thumb, the gripping portions may comprise one segment adapted to look like the distal phalanx (the stabiliser and knuckle connector being adapted to look like the metacarpal member and proximal phalanx) or the thumb may alternatively comprise two segments corresponding to proximal and distal phalanges. However, it will be appreciated that the gripping members may comprise any number of phalanges without departing from the scope of the invention. It is not essential that the gripping members simulate the appearance of a human hand.

In one embodiment, shown in FIG. 1, the gripping members are in the form of four fingers 2a, 2b, 2c, 2d and a thumb 2e, each extending from a respective metacarpal member. Each gripping member comprises a plurality of gripping portions joined together to resemble the fingers or thumb (as the case may be) of a human hand. In particular, each finger gripping member comprises a first gripping portion that forms a proximal phalanx, which is attached to the respective metacarpal member via a metacarpophalangeal joint. The proximal phalanx 10 of the gripping member is the phalanx located closest to the metacarpal member and to which the respective stabiliser and actuator arm are attached.

The gripping members corresponding to the fingers of the hand also comprise a second gripping portion in the form of a middle phalanx 11 and a third gripping portion in the form of a distal phalanx 12. The middle phalanx is located between the proximate phalanx and distal phalanx, the distal phalanx being located at the distal end of the gripping member.

In one form, the middle phalanx 11 and distal phalanx 12 are joined together in a fixed position. In the embodiments shown in FIGS. 1, 2, 7, and 10, the middle and distal phalanges are integral with each other and are formed as a single part. The distal phalanx is angled from the middle phalanx to form a curled finger section that substantially simulates the angle between the middle and distal phalanges of a human finger when in a relaxed state. The curled arrangement makes it easier for the finger to grip an object, especially a curved object. Because the middle and distal phalanges are in a fixed position relative to each other, movement of the middle phalanx causes simultaneous movement of the distal phalanx.

In one form, each gripping member is adapted to move by the use of one or more linkages or other suitable joints (such as an arrangement using pulleys and cable, for example) that directly or indirectly attach the metacarpal member to at least the first gripping portion or proximal phalanx. One or more linkages or other suitable joints may also attach the proximal, middle, and distal phalanges together so that the phalanges can move relative to each other.

In one form, as shown in FIGS. 2, 7, 8, 10, 12, 14, and 16, the first gripping portion (the proximal phalanx 10) of the gripping members corresponding to fingers 2a, 2b, 2c, 2d is attached to the actuator via a joint comprising a parallel linkage 15, which is adapted to transfer linear motion from the actuator into radial motion of the gripping member, to allow the gripping member to contract and curl or to flex and extend. This movement allows the automated hand to grip and release objects in a similar way to a human hand.

A first end of the parallel linkage 15 is rotationally attached to the metacarpal member 3 via the knuckle connector 9 and via the transfer joint 14. The second, opposing end of the parallel linkage 15 is rotationally attached to the adjacent phalanx or gripping portion—in this case, the middle phalanx 11 of a finger. The gripping member corresponding to the thumb may optionally be formed in the same way if the thumb is adapted to comprise two or more phalanges.

The parallel linkage 15 comprises a pair of first 16 and second 17 elongate links having opposing first and second ends. The parallel linkage also comprises a third link 18 and a fourth, spacer link 19.

Figure 22:
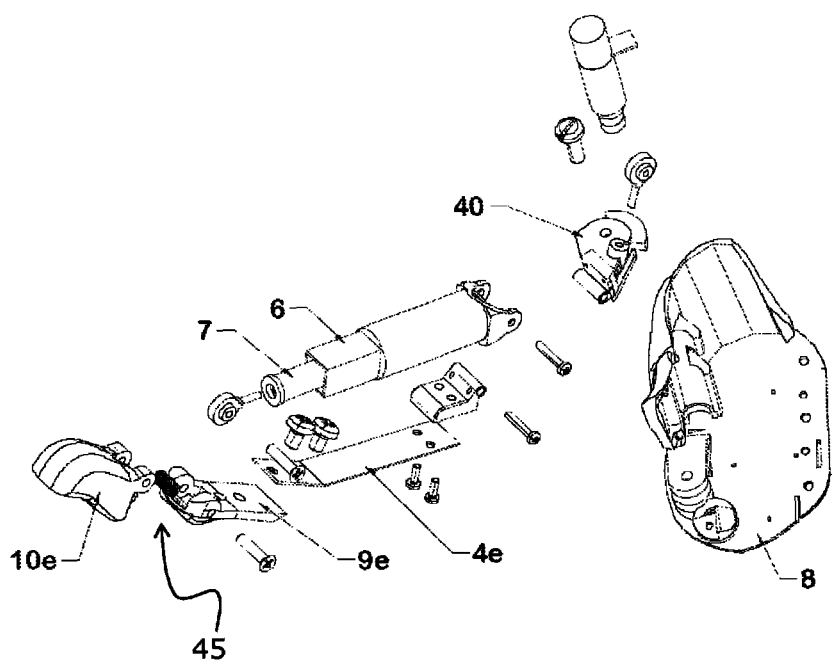
FIG. 22 is an exploded view of thumb components according to another form of the invention.

The first and second links move and change position with respect to each other as the gripping member curls and extends. However, when the hand is in the neutral, rest position, as shown in FIGS. 21 and 22, the first and second links 16, 17 of the parallel linkage are substantially parallel. Therefore, the first and second links are collectively referred to hereafter as 'parallel links'.

Referring to FIG. 2, the first end of the first parallel link 16 is rotationally attached to the knuckle connector 9 via a hinged joint 9a, as described above, so that the first link can pivot about the distal end of the metacarpal member. In particular, an aperture 22a, at the first end of the first link 16 is aligned with an aperture 18a at the first end of the third link 18 and is also aligned with an aperture 9a on the knuckle connector 9 of the metacarpal member 3. A pivot shaft 26 extends through the aligned apertures 22a, 18a and 9a to allow the first link 16 to pivot about the shaft 26 to pivot about the knuckle connector 9.

The first end of the second parallel link 17 is rotationally attached to the second end of the third link 18, which attaches the second link to the knuckle connector 9. The first end of the second link 17 and the second end of the third link 18 rotationally attach the second and third links to the distal end of the actuator arm via the transfer joint 14. The transfer joint is adapted to allow the third link 18 to pivot about the distal end of the actuator arm 5. In particular, an aperture 23a at the first end of the second link 17 aligns with an aperture 20 at the second end of the third link 18. A pivot shaft 32 extends through the aligned apertures 23a, 20, allowing the second link 17 and third link 18 to pivot about the shaft 32. The parallel linkage arrangement therefore attaches to the stabiliser and actuator arm of the metacarpal member to form a metacarpophalangeal joint about which the gripping member can curl and flex.

The second ends of the first and second link 16, 17 are rotationally attached to the middle phalanx 11 via a hinged joint. In particular, an aperture 22b in the second end of the first parallel link 16 is aligned with a corresponding first aperture 25a located at a first end near the contact surface of the middle phalanx. Similarly, an aperture 23b in the second end of the second parallel link 17 is aligned with a corresponding second aperture 25b located at the first end near the upper surface of the middle phalanx. A pivot shaft 27a, 27b is located between each pair of aligned apertures in such a way that the proximal and middle phalanges are able to pivot about the shafts 27a, 27b so that the finger can curl and flex.

In this form of the invention, the parallel linkage forms the first gripping portion or proximal phalanx of the finger and the metacarpophalangeal joint allows the proximal phalanx to curl and flex to simulate the movement patterns of the proximal phalanx of a human finger.

The joint arrangement between the proximal and middle phalanges forms a proximal interphalangeal joint that allows the middle phalanx to pivot relative to the proximal phalanx to simulate movement patterns of the middle phalanx of a human finger.

As shown in FIGS. 7, 8, 10, 12, 14, and 16, the parallel linkage 15 may also comprise a biasing means 21 having first and second ends, the first end attaching to the first parallel link 16 and the second end attaching to the second parallel link 17. Preferably, the biasing means is a leaf spring.

The biasing means 21 helps to hold the finger in the default rest position, unless resistance is encountered, in which case it provides gauge tension that determines when the middle phalanx begins to curl. In this way, the middle and distal phalanges are caused to curl before the proximal phalanx. The biasing means may be in the form of a spring, elasticated band, or any other suitably flexible and resilient form.

The hand is operated by a control system, which may be attached to the support frame or otherwise located in the base of the hand or in the lower arm/wrist region behind the base of the hand (not shown). The control system may be programmed to control movement patterns of the metacarpal members and gripping members of the entire hand and/or individual control systems may be utilised to control different metacarpal members and gripping members. The control system receives signals from sensors positioned on the lower arm/wrist portion and transmits these signals to the relevant actuator(s).

Figure 7:
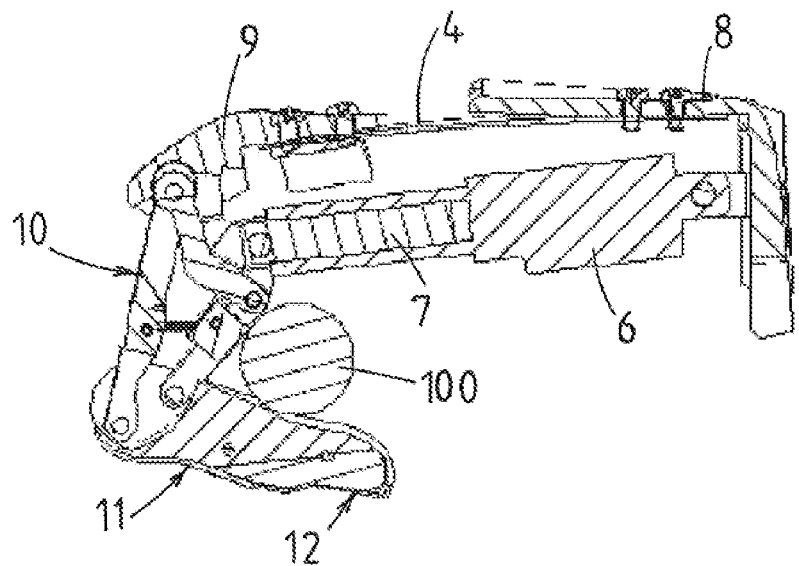
FIG. 7 is a cross-sectional view taken along line B-B of FIG. 6 and in which the finger is gripping an object.

To manipulate a gripping member so that it curls to form a gripping position, the respective actuator receives an actuation signal from the control system, instructing the actuator to cause the gripping member to curl. The drive system then causes the actuator arm 7 to retract toward the support frame 8 at the base of the hand, as shown in FIG. 7. As the actuator arm 7 retracts, it pulls the parallel linkage 15 toward the support frame at the base of the hand by pulling on the fourth link 19 that is rotationally attached to the actuator arm 7 via the transfer joint 14. The fourth link pulls on the second parallel link 17. The first parallel link 16 is attached to the second parallel link 17 via the third link 18 and via the middle phalanx. Thus, as the actuator arm retracts and the second parallel link is pulled toward the support frame 8 at the base of the hand, the first parallel link 16 is caused to move toward the support frame. In this way, the retracting actuator arm 7 pulls the proximal phalanx toward the actuator, causing the proximal phalanx to curl.

As the actuator arm retracts further, the second parallel link 17 is pulled further toward the support frame 8, which pulls the middle phalanx in the same direction, causing the middle phalanx to pivot about the interphalangeal joint. Therefore, the retracting actuator arm causes the middle phalanx to curl toward the palm of the hand.

Arrow I in FIG. 8 illustrates the path of rotation of a gripping member corresponding to a finger. In this form, the curved or angled gripping member simulates a curled human finger that curls and flexes.

Figure 13:
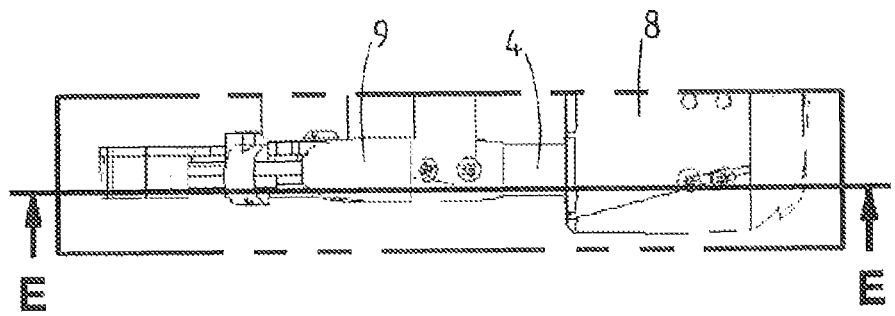
FIG. 13 is a top view of the finger of FIGS. 11 and 12, the finger being in a partially extended position.
Figure 14:
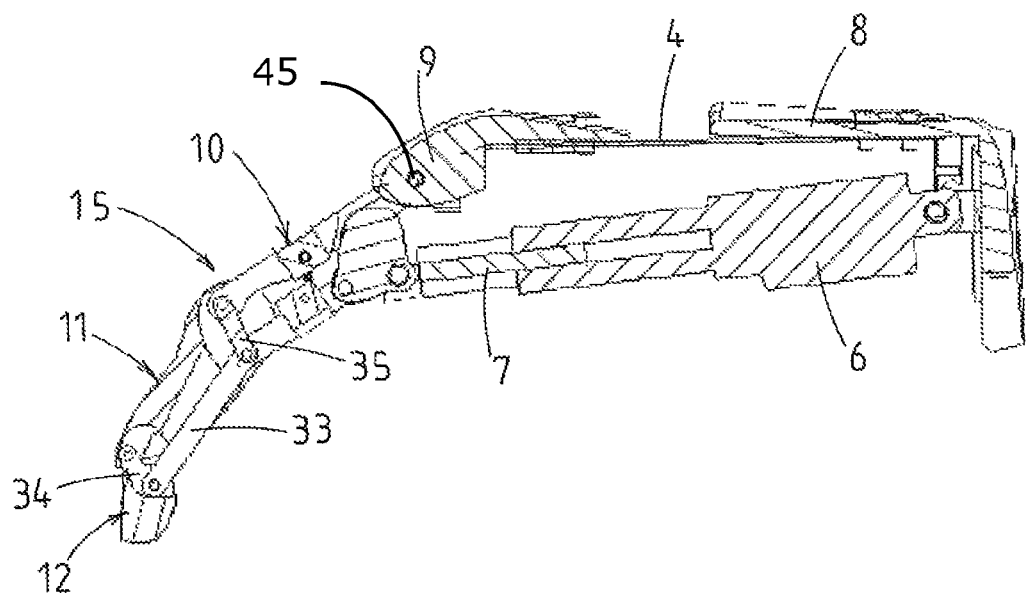
FIG. 14 is a cross-sectional view of a finger taken along line F-F of FIG. 13.

Conversely, if the control system instructs a gripping member 2 to flex, the actuator arm 5 will extend away from the support frame 8. As the actuator arm begins to extend, the fourth link 19, which is attached to the actuator arm via the transfer joint 14, moves toward the second parallel link 17 and pushes the second parallel link 17 away from the actuator arm, and support frame 8. The second link 17 pushes the bottom portion of the middle phalanx away from the actuator arm and support frame, which in turn pushes the distal phalanx away also. Thus the proximal phalanx 10 comprising the parallel linkage 15, and the attached middle phalanx 11 and distal phalanx 12 are caused to flex away from the palm of the hand, as shown in FIGS. 13 and 14.

As the proximal and middle phalanges 10, 11 curl, the flexible stabiliser 4 moves toward the actuator and away from its neutral, rest position. The support frame 8 at the base of the hand may also be caused to flex with the stabilising member. This movement is illustrated by broken lines in FIGS. 7, 10, 12, and 14.

When the hand returns to its neutral, rest position, the resilient characteristics of the flexible stabilisers allow the stabilisers and the support frame to resume the neutral, rest position. The use of a metacarpal bracket and a flexible brace may also help the stabilisers to resume the neutral, rest position.

In another form, as shown in FIGS. 11 to 14, the middle and distal phalanges are rotationally attached via a second linkage system that allows the middle and distal phalanges to move independently relative to each other in a similar way to that of a human finger. In this form, the distal end of the middle phalanx is rotationally attached to a first end of the distal phalanx so that the distal phalanx can pivot up and down relative to the middle phalanx. The second linkage comprises an elongate linking arm 33 that is rotationally attached to the distal phalanx, either directly or by attaching to a distal link 34 that is itself rotationally attached to the distal phalanx. In one form the distal phalanx comprises an angled distal link 34 having one end rotationally attached to the linking arm 33 and another end rotationally attached to the distal phalanx 12 near the contact surface of the distal phalanx. The linking arm 33 is rotationally attached at one end to the distal phalanx 12 and angled link 34 and is rotationally attached at its other end to the middle phalanx 11 and second parallel link 17. The linking arm is also rotationally attached to a drive link 35, having a first end that is rotationally attached to the first parallel link 16 and a second end that is rotationally attached to the second parallel link 17. In this arrangement, movement of the parallel linkage causes movement of the proximal, middle, and distal phalanges. FIGS. 11 to 14 show movements of the gripping member 2 where the distal phalanx is moveable relative to the middle phalanx.

Figure 12:
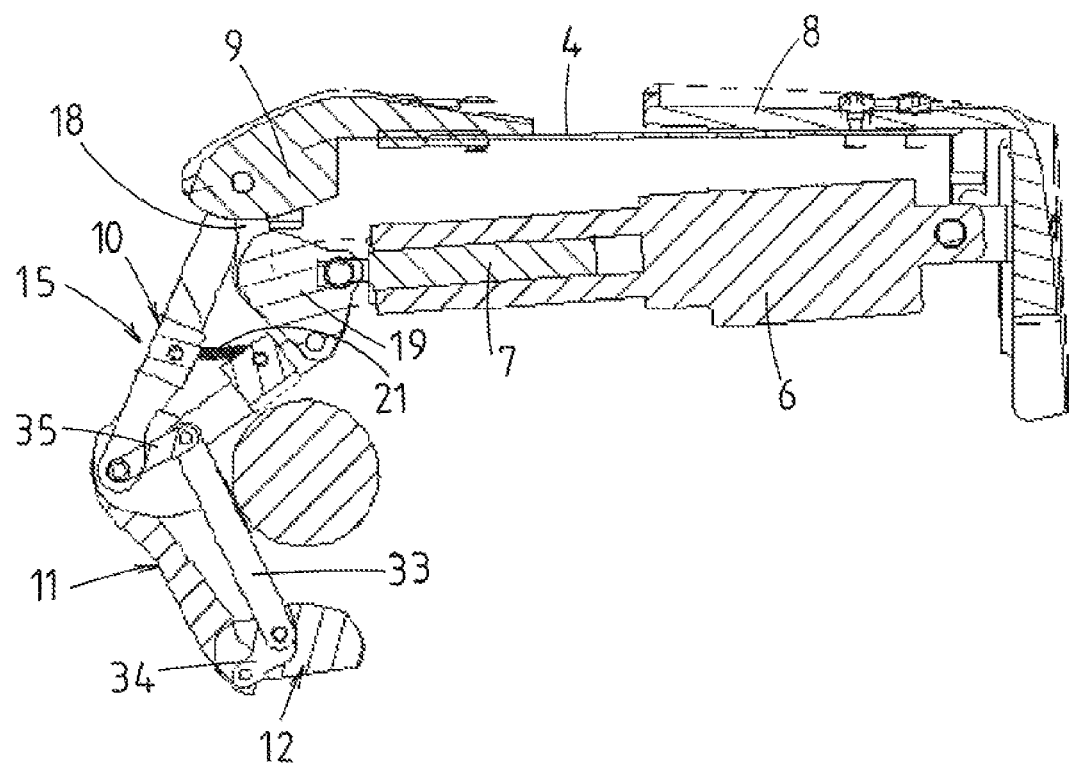
FIG. 12 is a cross-sectional view of the finger of FIG. 11 taken along line E-E where the finger is in a partially curled position.

For the gripping member to curl, the actuator arm 7 retracts toward the support frame 8, pulling the second parallel link 17 and the linking arm 33 toward the support frame. The movement of the second parallel link 17 toward the support frame causes the proximal and middle phalanges to curl, as described above. As the linking arm 33 is pulled toward the support frame, the linking arm pulls on the distal phalanx 12, causing the distal phalanx to curl, as shown in FIG. 12. Therefore, all three phalanges are able to curl toward the palm of the hand.

Conversely, extension of the actuator arm 7 causes the second parallel link 17 to be pushed away from the support frame 8 and palm of the hand. The linking arm 33 links the parallel linkage to the distal phalanx 12. Thus, as the second parallel link 17 is pushed away from the support frame 8, the linking arm 33 is pushed in the same direction. The linking arm is rotationally attached to the distal phalanx 12 near the contact surface of the distal phalanx. So, as the linking arm is pushed away from the support frame, causing the distal phalanx to flex with respect to the proximal phalanx 10 and the middle phalanx 11, as shown in FIG. 14. Therefore, the gripping portions of the gripping members are able to curl and grip an object and are also able to flex and release an object from their grip.

In one form, the second and third gripping portions of a gripping member are joined together in a curved or angled arrangement. The distal phalanx therefore moves simultaneously with the middle phalanx. For example, as shown in FIGS. 1, 2, 7, 8, and 10, the distal phalanx is integral with the middle phalanx and is joined with the middle phalanx in an angled arrangement in which the distal phalanx is angled further toward the palm of the hand than the middle phalanx. When the proximal and middle phalanges curl toward the palm of the hand, the distal phalanx also curls toward the palm of the hand to form a gripping position. In this curled gripping position, the gripping member is able to grip an object 100, as shown in FIGS. 7, 12 and 25.

When each gripping member moves, the actuator may move up and down toward and away from the stabiliser to accommodate movement of the finger. The ability of the actuator to pivot up and down toward and away from the stabiliser is provided by the universal joint 13 where the actuator attaches to the support frame at the base of the hand, and is also provided by the ability of the stabilisers to flex up and down toward and away from the actuator.

It is not essential for all gripping members to use the same form of actuator. For example, in one form of the invention, two or more gripping members can move simultaneously using the same actuator. Optionally, at least one gripping member is adapted to move as a result of movement of another gripping member, the two gripping members being attached in a way that results in substantially simultaneous movement.

Figure 18:
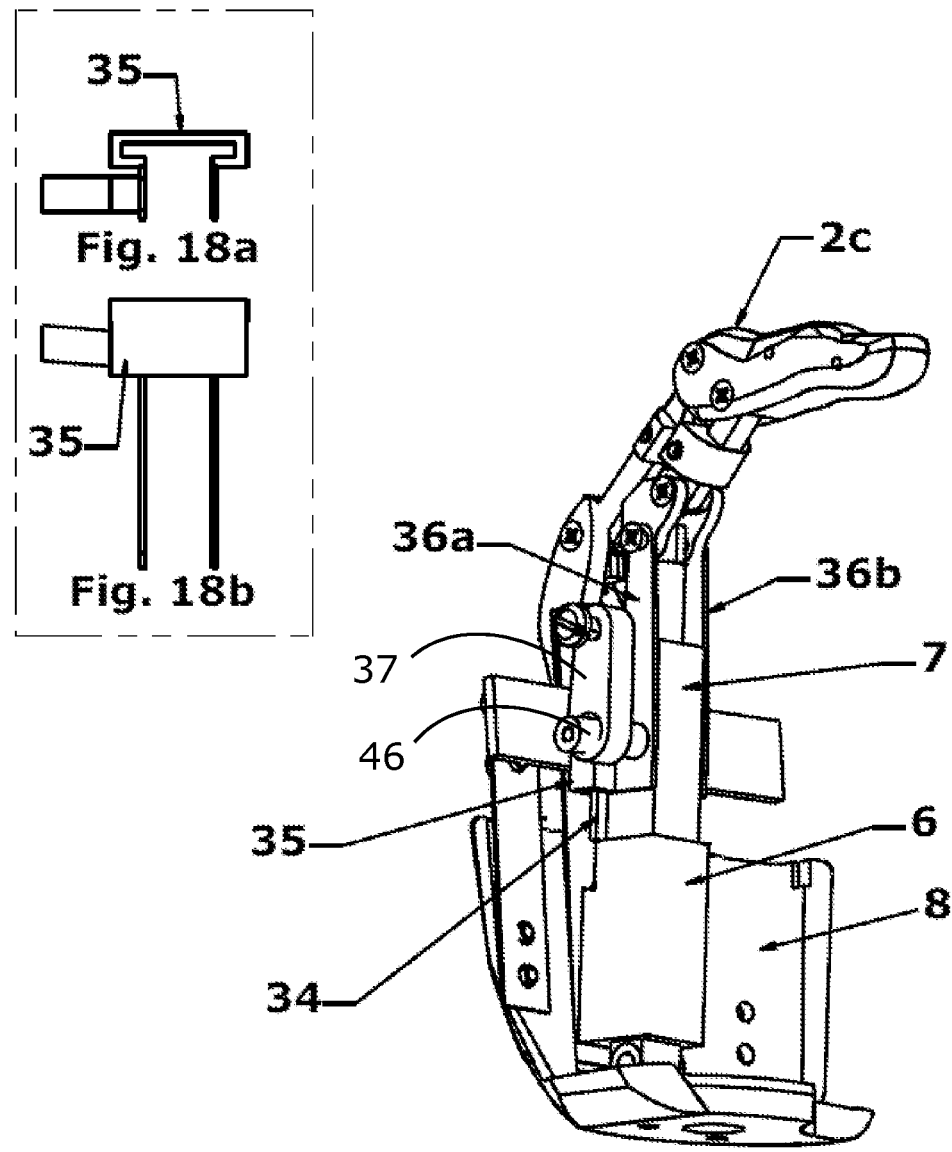
FIG. 18 is a perspective view of a control finger comprising one form of simultaneous movement actuation system according to the invention.
Figure 19:
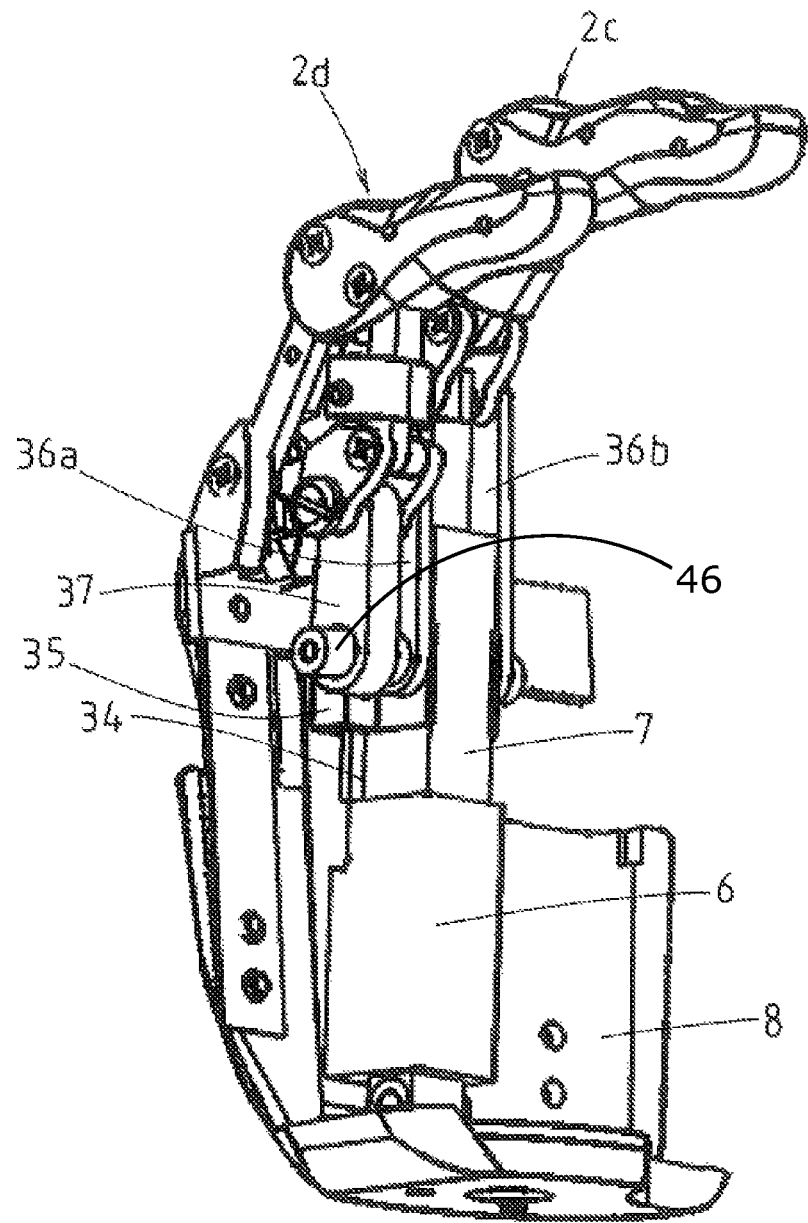
FIG. 19 is a perspective view showing a control finger and a subsidiary finger comprising one form of simultaneous movement actuation system.

One form of simultaneous actuation system is shown in FIGS. 18 and 19 in which a gripping member 2 (forming a control finger) attaches to a metacarpal member having a stabiliser and actuator, as described above. An adjacent gripping member (forming a subsidiary finger) also attaches to a metacarpal member having a stabiliser but using the actuator of the control finger to cause the subsidiary finger to curl and flex. The control finger (in this case the ring finger) and adjacent subsidiary finger (in this case the little finger) together comprise a simultaneous movement actuation system adapted so that movement of the control finger causes simultaneous movement of at least one adjacent subsidiary finger, in this case the little finger.

The simultaneous movement actuation system comprises a transfer means that is operably engaged with the control finger and subsidiary finger so that both fingers move simultaneously. In one form, the transfer means comprises a guide rail, sliding frame, and a transfer arm. The guide rail 34 runs along the length of the actuator housing 6 and is preferably positioned on the surface of the actuator housing facing the stabiliser, although the guide rail could be positioned at any suitable location.

The transfer means also comprises a frame 35 slidably attached to the guide rail 34, such that the sliding frame 35 is capable of sliding along the length of the guide rail. The sliding frame 35 is shaped to clamp onto the guide rail in a sliding arrangement. The guide rail 34 is formed from a pair of elongate flanges, each flange extending from opposing sides of the actuator housing, as shown in FIGS. 18 and 19. The sliding frame 35 is shaped so that, from an end view, the interior of the sliding frame is T-shaped to allow at least part of the actuator housing 6 and the guide rails 34 to fit within the hollow T-shaped interior, as shown in FIG. 18a. The rear of the sliding frame is substantially flat, as shown in FIG. 18b, so as not to interfere with nearby components of the automated hand.

The sliding frame comprises at least one connecting arm that is attached to the first gripping portion of the control finger. In the embodiment illustrated in FIGS. 18 and 19, the sliding frame comprises a pair of first and second connecting arms 36a, 36b that attach the sliding frame 35 to the first gripping portion 10 (proximal phalanx) of the control finger 2c. In one form, the connecting arm(s) is/are attached to the fourth link 19 of the parallel linkage 15, forming the proximal phalanx 10 of the control finger. In this arrangement, the fourth link 19 is able to pivot about the connecting arms 36a, 36b, although the connecting arms themselves maintain a fixed position relative to the sliding frame.

The transfer arm 37 transfers movement of the control finger to the subsidiary finger. At a first end, the transfer arm 37 is attached to the sliding frame 35 and/or to the adjacent connecting arm 36a. The substantially opposing second end of the transfer arm 37 is rotationally attached to the proximal phalanx of the subsidiary finger, preferably by attaching to the fourth link 19 of the proximal phalanx parallel linkage. The fourth link of the proximal phalanx parallel linkage is able to pivot about the second end of the transfer arm.

In operation, as the actuator arm 7 of the control finger extends and pushes against the gripping member, the linear extension of the actuator arm causes the phalanges of the control finger to extend and flex, as described above. The sliding frame 35 and the connecting arm(s) 36a, 36b of the sliding frame are caused to slide along the guide rail 34 in the direction of the extending actuator arm. Simultaneously, as the sliding frame 35 moves in the direction of the actuator arm 7 and gripping member, the transfer arm 37 is caused to move in the same direction. The transfer arm 37 then functions in the same way as the actuator arm 7, by pushing against the proximal phalanx 10d of the subsidiary finger 2d, causing the phalanges of the subsidiary finger to flex, as described above.

To curl the control finger and subsidiary finger, the actuator arm retracts, as described above, causing the sliding frame and transfer arm to move in the same direction, thereby pulling on the proximal phalanx of the subsidiary finger so that both the control finger and the subsidiary finger curl simultaneously.

Although simultaneous movement of a control finger and only one adjacent finger is described, it is possible to use two transfer arms (one attached to each side of the sliding frame) to cause simultaneous movement of adjacent fingers on each side of the control finger.

As described above, the automated hand may comprise at least one gripping member corresponding to a thumb, which is attached to the support frame at the base of the hand such that the thumb substantially opposes at least one of the fingers of the hand. In other words, the thumb is positioned on the hand so that it can curl toward the finger(s) and the finger(s) can curl toward the thumb.

As described above, the thumb comprises a metacarpal member comprising a stabiliser 4e and an actuator 5. The metacarpal member is attached to the support frame via a universal joint and is adapted to move up, down and laterally relative to the support frame. The metacarpal member of the thumb is also rotationally attached to a gripping member 2e.

Also as described above, the thumb stabiliser is preferably formed of spring steel that is springloaded to a rest position. This means that the stabiliser can move up and down and laterally relative to the support frame and can also twist to some extent under the effect of external forces, but the resilient nature of the springloaded stabiliser will encourage the stabiliser to resume its natural, rest position once external forces are removed. The ability of the stabiliser (and metacarpal member) to move so as to withstand forces in all directions, substantially improves the robustness of the thumb.

In one form, the thumb comprises an angled stabiliser 4e having one end that is angled toward the actuator 5e. The angled end of the stabiliser 4e is attached to a knuckle connector 9e that attaches to the gripping member 10e, by attaching to the first gripping portion of the thumb. The gripping member is rotationally attached to the distal end of the actuator arm 7e via a transfer joint 14 and to the knuckle connector 9e via a hinged joint 45 to form a metacarpophalangeal joint, as described above. In this form, as described above, linear retraction and extension of the actuator arm causes the thumb gripping member 10e to curl and flex.

In one form, as shown, the thumb gripping member 2e comprises a single moveable gripping portion or phalanx shaped to look like a distal phalanx, the knuckle connector being shaped to look like a proximal phalanx. In another form, the thumb comprises a plurality of phalanges attached together using a linkage arrangement as described above or using any other suitable joint arrangement that allows the phalanges to curl and flex.

Figure 23:
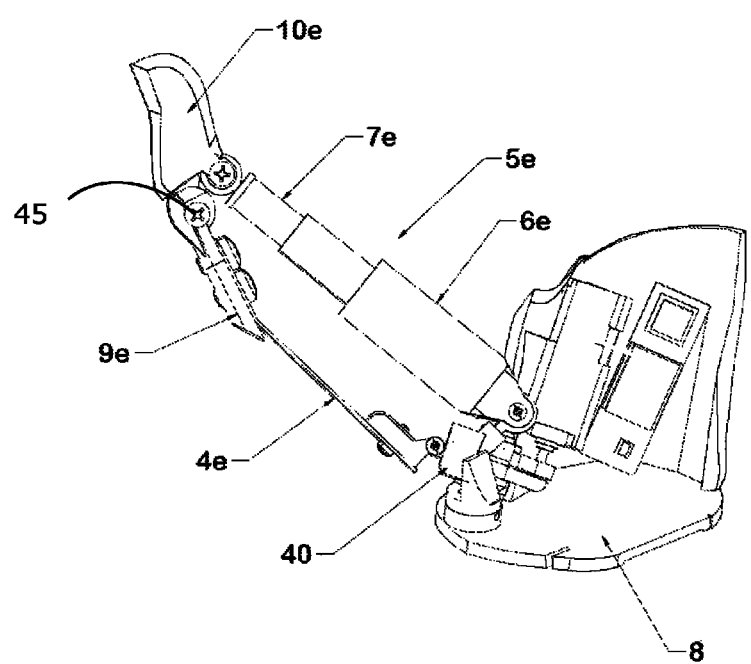
FIG. 23 is a perspective view of the assembled thumb of FIG. 22 attached to a support frame.

In one form, as shown in FIGS. 20 to 23, the thumb comprises an actuator comprising a linearly extending and retracting actuator arm 5, a housing 6 and a drive system comprising a motor. The actuator arrangement is the same as that described above where the housing houses the motor and has an opening at one end through which the actuator arm extends and retracts. The actuator is rotationally attached to a swiveling mounting block 40 via a hinged joint so that the actuator can pivot up and down relative to the support frame, as described above. The swiveling mounting block is rotationally attached to the support frame 8 at the base of the hand so that the mounting block (and actuator arm and thumb gripping member) is able to pivot laterally by swiveling in an arc. Optionally, the swiveling mounting block sits in a recess within the support frame to provide an anatomical alignment that is similar to that of a human hand. The thumb may be positioned so that when the swiveling mounting block rotates, the thumb is caused to rotate about an axis that is between approximately 20 and 70 degrees to the palm of the hand, as shown in FIG. 23.

The thumb stabiliser 4e is also attached to the swiveling mounting block. Therefore, the thumb metacarpal member, comprising a stabiliser and actuator, is rotationally attached to the support frame via the swiveling mounting block, which acts as a universal joint.

The swiveling mounting block 40 is adapted to house a servomotor to independently control the ability of the thumb to swivel laterally. As with the fingers of the hand, the ability of the actuator to cause the thumb to move up and down is controlled by the actuator motor, which is held within the actuator housing, as described above. Because the actuator motor forms part of the actuator and can move up, down, and laterally, there is little risk of damage to the actuator motor if the thumb is impacted.

The thumb is therefore able to pivot up and down relative to the support frame and can also pivot laterally in an arc to substantially simulate thumb movement in a human hand.

The ability of the thumb to move laterally allows it to be squeezed laterally and to receive at least some lateral impact forces without damaging the thumb.

As mentioned above, the automated hand of the present invention may assume a default, neutral, rest position that may simulate the rest position of a human hand. In the default, rest position shown in FIG. 24, each actuator 5 is slightly extended and each gripping member is slightly curled. When the hand assumes the rest position, a gently curved imaginary line N is formed across the metacarpal members 3 that form the back of the palm of the hand and knuckle connectors 9. However, the metacarpal members can also move out of the neutral position to mould the hand around an object 100 so that the hand can grip the object, as shown in FIG. 25. In this illustration, the automated hand is gripping a ball 100. The metacarpal members 3 of the hand are able to mould themselves around the ball as the actuators 5 pivot around the universal joint 13.

The actuators 5a, 5c, 5d of the index finger 2a, ring finger 2c and little finger 2d are able to move away from the respective stabilisers 4a, 4c, 4d, and toward the object 100 being held by rotating about the universal joint 13. The flexible, resilient stabilisers 4a, 4c, 4d are consequently pulled in the same direction, causing each metacarpal member 3a, 3c, 3d to independently move out of its neutral, rest position to mould around the object, as indicated by broken line N in FIG. 25.

Each metacarpal member is also able to move upwardly, as the actuators move upwardly from the universal joint toward the stabilisers, causing the stabilisers to move in the same direction. For example, as shown in FIG. 25, to accommodate the full curvature of the ball 100, the actuator 5b of the middle finger 2b pivots toward the respective stabiliser 4b, causing the metacarpal member 3b of the middle finger to move upward and out of the neutral, rest position.

In this way, the hand comprises metacarpal members that are independently movable up and down and laterally, providing a hand that is capable of substantially moulding itself around an object. Where the hand has a plurality of fingers, the metacarpal members of the fingers are able to form a compliant palm by way of their ability to move up, down, and laterally so that the palm is able to substantially mould around an object gripped by the hand.

Figure 26:
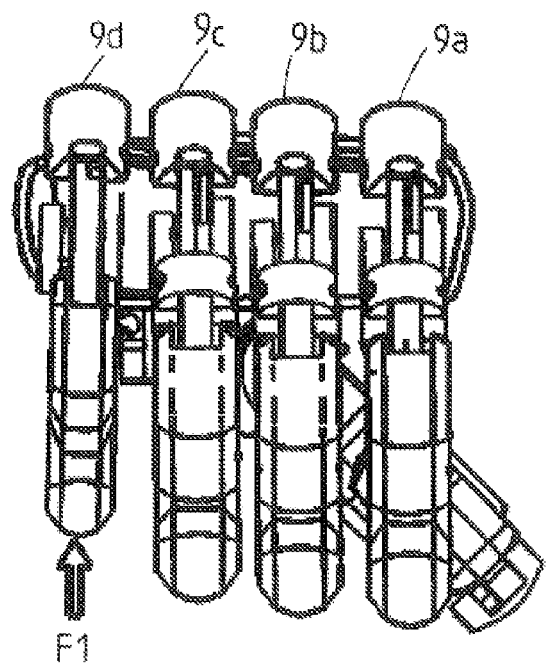
FIG. 26 is a front view of a hand according to one form of the invention in which the tip of a gripping member is subjected to a longitudinal force.
Figure 27:
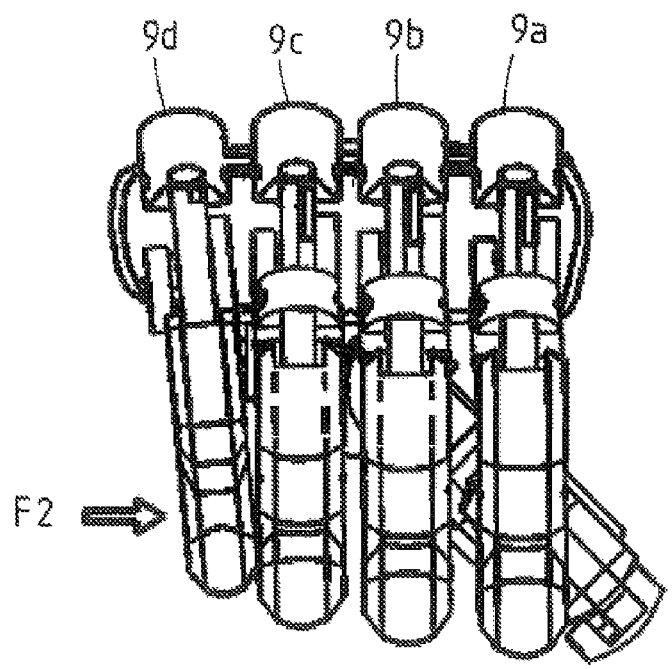
FIG. 27 is a front view of a hand according to one form of the invention in which a gripping member is subjected to a lateral force.

Each metacarpal member may also be adapted to move when longitudinal and/or lateral impact forces are applied to its respective gripping member, as shown in FIGS. 26 and 27. For example, when a longitudinal impact force F1 strikes the distal end of a gripping member 2, the gripping member moves in the direction of the force, causing the respective metacarpal member 3 to move in the direction of the force also, as shown in FIG. 26. Because each stabiliser is made of a flexible, resilient material, the stabiliser is able to move in the direction of the force. Similarly, because the actuators 5 are attached to the support frame 8 via a universal joint 13, the actuator 5 is able to move upwardly in the direction of the force also. Thus, when an impact force strikes the distal end of a gripping member, the compliant nature of the palm of the hand allows for some of the force to dissipate and reduces the likelihood that the hand will sustain significant damage as a result of the impact.

After the force is removed, the resilient nature of the spingloaded stabilising members causes the metacarpal members to resume their default, neutral rest position. The flexible brace also helps the metacarpal members to return to their neutral positions. When the hand is in the default, rest position, the metacarpal members are in an "untensioned" neutral position. In this position, the metacarpal members are at their most flexible if laterally impacted. As a grip resistance applies pressure on the metacarpal member, the resistance of the metacarpal member increases according to its resilience properties. This reduces the range of lateral flexibility and instead provides a required firmness for gripping objects, especially curved objects or small objects.

The universal joint 13 (that allows the metacarpal members to pivot vertically and laterally), allows each gripping member to sustain a degree of lateral movement without significant damage to the gripping member or hand. For example, as shown in FIG. 27, when a lateral force F2 strikes a finger of the hand, such as the little finger, the finger is able to move in the direction of the force to some extent to dissipate some of the force. This movement is provided by the flexibility of the stabilisers and by the universal joint to which the actuating member is attached. Where the little finger uses a simultaneous actuation system, as shown in FIGS. 18 and 19, the transfer arm that attaches the little finger to the ring finger may be attached to the sliding frame 35 via a shaft that provides a slippage linkage 46 such that of the lateral force causes the little finger to hit the transfer arm 37, the transfer arm can slide along the shaft toward the ring finger to help dissipate the force and reduce damage to the fingers of the hand. Thus, again, the metacarpal members are adapted to move independently to absorb and dissipate the force to some extent.

To provide further support and security to the components of the hand, and to improve the natural look of the hand, the hand may comprise a stretchy or flexible membrane or skin covering its outer surfaces. Optionally, the contact surface of the palm and on the contact surfaces of the gripping members may comprise a textured or tacky/sticky material to assist in the gripping of an object.

Although the invention has been described in relation to an automated hand for a prosthetic, the invention may equally be employed as a gripping device for a robotic arm.

Advantages of the Invention

The invention offers significant advantages in the gripping ability of the hand compared to known automated hands. By providing a hand having metacarpal members and gripping members that move up, down, and laterally, the hand is better able to grip an object. Where metacarpal members of the hand comprise a palm, the movement ability of the metacarpal members allow the palm to be a compliant palm that is able to curve around an object in both the lateral and longitudinal directions so that the hand is better able to grip an object by moulding around the object to some extent. In addition, the moveable nature of the thumb provides the hand with improved gripping abilities.

Furthermore, because the stabilisers and actuating members are able to move laterally, the finger metacarpal members that form a palm are able to spread apart from each other to increase the surface area of the palm of the hand, which provides the hand with a greater ability to grip an object.

The ability of the metacarpal members and the gripping members to move laterally, improves the robustness of the hand by helping the hand to dissipate impact forces to reduce the likelihood that an impact will cause significant damage to the hand. Similarly, the hand can be squeezed to some extent without risking damage.

The movement characteristics of the automated hand of the present invention also allow the hand to substantially simulate the movement of a human hand, resulting in a more natural looking prosthetic.

The hand may also be more cost efficient where a simultaneous movement actuation system is used because, under this system, only one actuator (comprising a motor) is used to move at least two gripping members.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. An automated hand comprising:
   a. a support frame;
   b. a plurality of metacarpal members, each comprising a proximal end rotationally attached to the support frame and a distal end rotationally attached to a gripping member, wherein the metacarpal members are adapted to pivot upwardly, downwardly, and laterally relative to the support frame; and
   c. one or more stabilisers each in the form of a resilient sheet and each having a first end attached to the support frame and a second end attached to a respective metacarpal member towards its distal end.

2. An automated hand according to claim 1, wherein each stabiliser is springloaded to a neutral rest position and adapted to flex upwardly, downwardly, and laterally relative to the support frame.

3. An automated hand according to claim 1, wherein each stabiliser attaches to a respective gripping member via a knuckle connector that angles the gripping member away from the stabiliser.

4. An automated hand according to claim 1, wherein at least two stabilisers form part of a metacarpal bracket having a base portion from which the stabilisers project and wherein the stabilisers are attached to the support frame via the base portion of the metacarpal bracket.

5. An automated hand according to claim 1, wherein a flexible brace extends across and is attached to the stabilisers.

6. An automated hand according to claim 1, wherein each metacarpal member comprises an actuator having a first end attached to the support frame and a second end attached to a respective gripping member via a hinged transfer joint, wherein the actuator is adapted to linearly extend and retract to cause the respective gripping member to pivot about the transfer joint.

7. An automated hand according to claim 6, wherein the actuator comprises an actuator arm and a drive system that engages with the actuator arm to cause the actuator arm to extend toward the gripping member and to retract away from the gripping member.

8. An automated hand according to claim 7, wherein a single actuator controls movement of at least one adjacent gripping member.

9. An automated hand according to claim 8, wherein a transfer arm is operably attached to a first gripping member comprising an actuator and is also attached to a second gripping member to transfer movement of the first gripping member to the second gripping member and wherein the second gripping member is adapted to slide laterally along the transfer arm.

10. An automated hand according to claim 6, wherein the gripping members comprise a plurality of gripping portions corresponding to a proximal phalanx, a middle phalanx, and a distal phalanx, wherein each metacarpal member is attached to the proximal phalanx of a respective gripping member and wherein the proximal phalanx comprises a parallel linkage adapted to control movement of the proximal phalanx and of an adjacent phalanx upon actuation of the actuator.

11. An automated hand according to claim 1, wherein a plurality of adjacent metacarpal members form a palm.

12. An automated hand according to claim 1, wherein at least one gripping member is a thumb being positioned on the hand to substantially oppose at least one other gripping member.

13. An automated hand according to claim 12, wherein the metacarpal member of the thumb is rotationally attached to a swiveling mounting block via a hinged joint and wherein the swiveling mounting block is rotationally attached to the support frame so that the mounting block forms a universal joint by which the metacarpal member of the thumb is attached to the support frame.

14. An automated hand according to claim 1, wherein the gripping members are adapted to move upwardly, downwardly, and laterally.

15. An automated hand according to claim 1, wherein each stabilizer is integrally formed with the support frame.

16. An automated hand according to claim 1, wherein each stabiliser is formed of a flexible resilient material.

17. An automated hand according to claim 16, wherein each stabiliser is formed of a material selected from spring steel, polypropylene, unexpanded polystyrene and PVC.

18. An automated hand comprising:
   a. a support frame;
   b. a plurality of metacarpal members, each comprising a proximal end attached to the support frame and a distal end attached to a gripping member, wherein the metacarpal members are adapted to pivot upwardly, downwardly, and laterally with respect to the support frame;

c. one or more stabilisers each having a first end attached to the support frame and a second end attached to a respective metacarpal member towards its distal end; and d. one or more flexible brace extending between one or more pairs of stabilisers towards the distal ends of each metacarpal member.

19. An automated hand as claimed in claim 18 wherein each stabiliser is formed of a flexible resilient material.

\* \* \* \* \*